United States Patent
Borad et al.

(10) Patent No.: US 9,750,741 B2
(45) Date of Patent: Sep. 5, 2017

(54) TARGETED THERAPIES FOR CANCER

(71) Applicants: THE TRANSLATIONAL GENOMICS RESEARCH INSTITUTE, Phoenix, AZ (US); MAYO FOUNDATION FOR MEDICAL EDUCATION AND RESEARCH, Rochester, MN (US)

(72) Inventors: Mitesh Jivraj Borad, Scottsdale, AZ (US); David Craig, Phoenix, AZ (US); John Carpten, Phoenix, AZ (US)

(73) Assignees: The Translational Genomics Research Institute, Phoenix, AZ (US); MAYO Foundation for Medical Education and Research, Rochester, MN (US)

( * ) Notice: Subject to any disclaimer, the term of this patent is extended or adjusted under 35 U.S.C. 154(b) by 49 days.

(21) Appl. No.: 14/776,552

(22) PCT Filed: Mar. 17, 2014

(86) PCT No.: PCT/US2014/030565
§ 371 (c)(1),
(2) Date: Sep. 14, 2015

(87) PCT Pub. No.: WO2014/145751
PCT Pub. Date: Sep. 18, 2014

(65) Prior Publication Data
US 2016/0038492 A1    Feb. 11, 2016

Related U.S. Application Data

(60) Provisional application No. 61/788,252, filed on Mar. 15, 2013.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *A61K 31/517* | (2006.01) |
| *A61K 31/5377* | (2006.01) |
| *C12Q 1/68* | (2006.01) |
| *A61K 9/00* | (2006.01) |
| *A61K 31/5025* | (2006.01) |
| *A61K 31/506* | (2006.01) |

(52) U.S. Cl.
CPC .......... *A61K 31/517* (2013.01); *A61K 9/0053* (2013.01); *A61K 31/506* (2013.01); *A61K 31/5025* (2013.01); *A61K 31/5377* (2013.01); *C12Q 1/6886* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 7,625,911 | B2* | 12/2009 | Huang | C07D 239/94 514/266.4 |
| 2010/0323957 | A1 | 12/2010 | Kuriyan | |
| 2011/0099644 | A1 | 4/2011 | Zhang | |
| 2012/0202763 | A1 | 8/2012 | Almstead | |
| 2012/0251530 | A1 | 10/2012 | Sliwkowski | |
| 2013/0064789 | A1 | 3/2013 | Falini | |
| 2013/0190310 | A1* | 7/2013 | Sidransky | C07K 16/18 514/234.5 |

OTHER PUBLICATIONS

Lubner et al. (Journal of Clinical Oncology, 2010, 28, 3491-3497).*
Zhang, ERRFI1, http://atlasgeneticsoncology.org/Genes/ERRFI1ID44147ch1p36.html, Apr. 2008 (retrieved from the internet on Apr. 13, 2017).*
Zhu et al. Development of Molecularly Targeted Therapies in Liliary Tract Cancers. Hetology. 2011, vol. 53(2), vol. 695-704. Abstract; and p. 693, col. 2, middle para, last.
Nagashima et al. Mutation of epidermal growth factor receptor is associated with MIG6 expression. FEBS J. 2009, vol. 276(18), p. 5239-51. Abstract.
Board et al> Integrated Genomic Characterization Reveals Novle, Therapeutically Relevant Drug Tarfets in FGFR and EGFR Pathways in Sporadic Intrahepatic Cholangiocarcinoma . . . .
International Search Report and Written Opinion of PCT application PCT/US2014/030565.

* cited by examiner

*Primary Examiner* — Dennis Heyer
*Assistant Examiner* — Daniel M Podgorski
(74) *Attorney, Agent, or Firm* — Rodney J. Fuller; Booth Udall Fuller, PLC

(57) ABSTRACT

Methods of selecting a chemotherapy regimen for treatment of cancer in a patient are disclosed. A patient genetic sample from a bilary cancer such as cholangiocarcinoma is analyzed for a mutation in ERRFI1 and a chemotherapeutic agent is selected as a result of the analysis. If a mutation in ERRFI1 is present, treatment with an inhibitor of Epidermal Growth Factor Receptor (EGFR) is shown to have inhibitory effects on tumor growth. In this manner, the chemotherapy regimen is targeted to a given mutation in a patient's cancer.

12 Claims, 13 Drawing Sheets

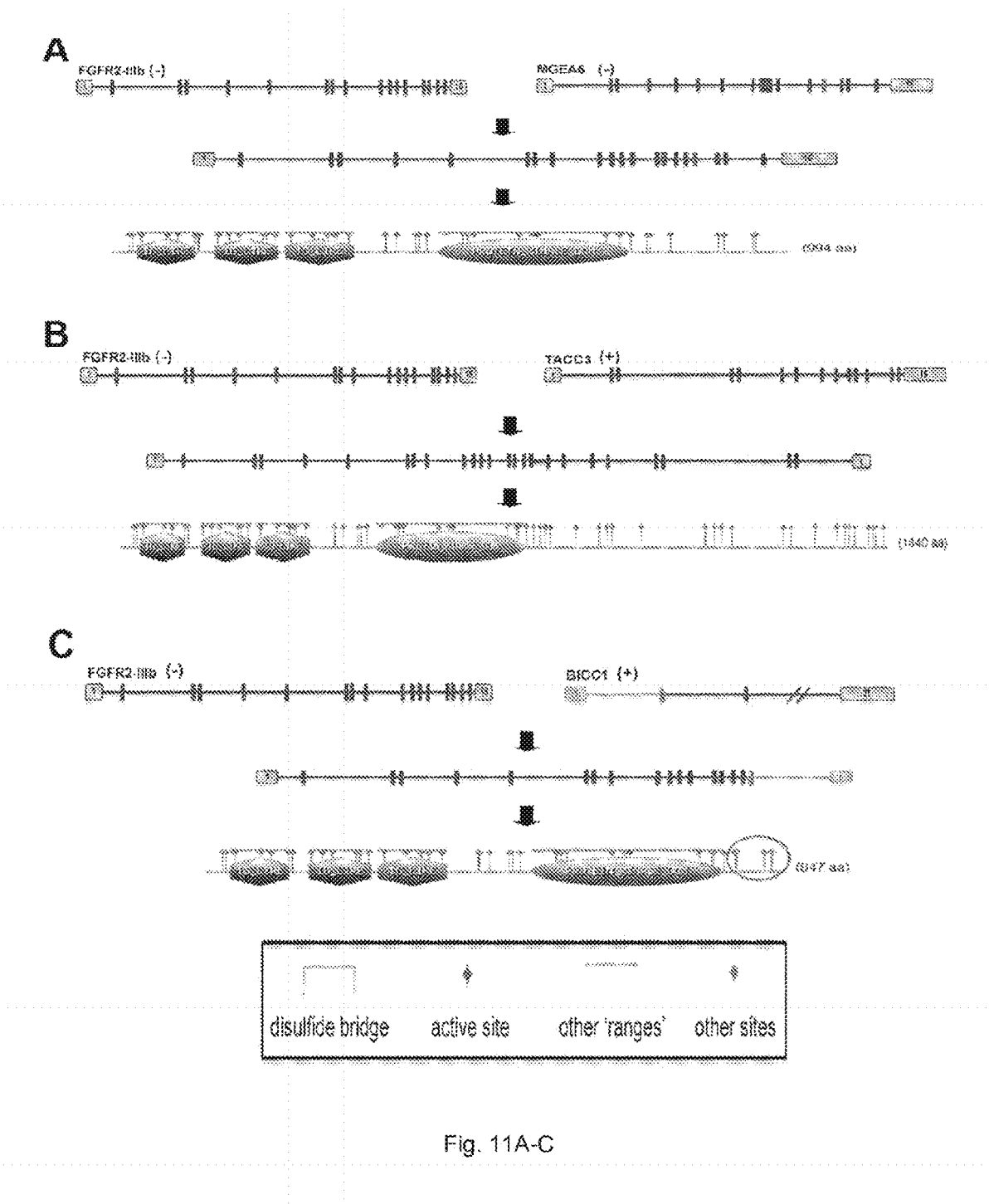
Fig. 11A-C

TARGETED THERAPIES FOR CANCER

CROSS-REFERENCE TO RELATED APPLICATIONS

The present application is the national stage of International Patent Application No. PCT/US2014/030565, filed on Mar. 17, 2014, which claims priority to U.S. Provisional Application Ser. No. 61/788,252 filed on Mar. 15, 2013, the contents of which is hereby incorporated by reference in its entirety.

FIELD OF INVENTION

The invention relates to methods for assessing and treating cancer, and in particular, biliary tract cancers, and most particularly, cholangiocarcinomas.

BACKGROUND OF THE INVENTION

Biliary tract cancers (BTC) comprise malignant tumors of the intrahepatic and extrahepatic bile ducts. Known risk factors for BTC are the liver flukes *O. viverrini* and *C. sinensis* in high prevalence endemic regions in southeast Asia [1]-[3], as well as primary sclerosing cholangitis [4]-[7], Caroli's disease [8], hepatitis B and hepatitis C [9]-[14], obesity [13], hepatolithiasis [15], [16] and thorotrast contrast exposure [17], [18]. Surgical approaches such as resection and liver transplantation represent the only curative treatment approaches for BTC [19].

Unfortunately, most patients present with surgically unresectable and/or metastatic disease at diagnosis. Systemic therapy with gemcitabine and cisplatin has been established as the standard of care for patients with advanced disease, but is only palliative [20], emphasizing the imminent need for novel therapies.

SUMMARY OF THE INVENTION

In some embodiments, methods for assessing and treating cancer in a patient are disclosed. A patient tumor sample from a cancer is analyzed for a mutation in ERRFI1. If a mutation is present, the patient is treated with an inhibitor of Epidermal Growth Factor Receptor (EGFR), such as erlotinib or gefitinib. Further assessment of the effects on the cancer may be accomplished through tomography following a course of treatment. Thus, methods for assessing and treating biliary tract cancer such as cholangiocarcinoma in patients having a mutation in ERRFI1 are described.

In other embodiments, methods for selecting a chemotherapy regimen for treatment of cancer are disclosed. After a tumor sample from a cancer patient is collected and analyzed for a mutations, a chemotherapeutic agent is selected. For example, an inhibitor of Epidermal Growth Factor Receptor (EGFR) is selected if an ERRFI1 mutation is present. In this manner, methods for selecting a chemotherapy regimen for treatment of biliary tract cancer such as cholangiocarcinoma in patients having a mutation in ERRFI1 are disclosed.

In yet other embodiments, uses of an EGFR inhibitor in the treatment of cancer, biliary tract cancer, and/or cholangiocarcinoma in a patient having a mutation in ERRFI1 are disclosed.

These and other aspects of the invention will be apparent upon reference to the following detailed description and figures. To that end, any patent and other documents cited herein are hereby incorporated by reference in their entirety.

Figure 6:
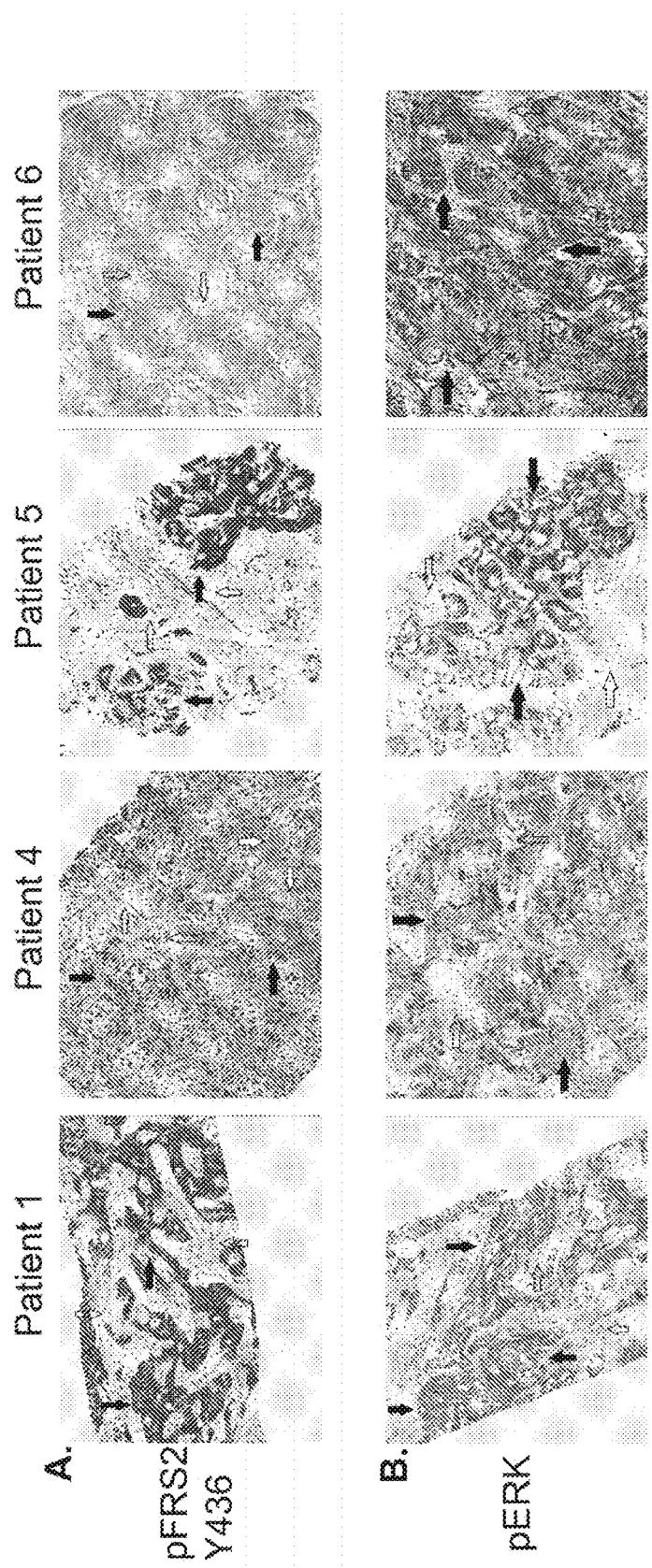

FIG. 6 depicts immunohistochemistry data demonstrating pFRS2 Y436, and pERK expression in Patients 1, 4, 5 and 6. A) Tumor stained with pFRS2 Y436 antibody. Patient 1 tumor cells demonstrating both strong cytoplasmic and nuclear expression of pFRS2 (solid arrows); background fibrous stroma is negative (empty arrows). Patient 4 tumor cells show strong nuclear expression and moderate to strong cytoplasmic positivity (solid arrows); occasional background fibrous stromal cells are negative for pFRS2 (empty arrows) and scattered tumor cells show basolateral/membranous staining as well (white arrows). Patient 5 tumor cells show intensely strong expression in both nuclei and cytoplasm (solid arrows); scattered background fibrous stromal cells are negative (empty arrows). Patient 6 tumor cells show negative nuclear expression of pFRS2, moderate cytoplasmic expression and basolateral or membranous expression of varying intensity (solid arrows); background fibrous stromal cells are negative (empty arrows). B) Tumor stained with pERK(MAPK) antibody. Patient 1 demonstrates negative/weak fibrous stroma (empty arrows) and tumor cells with negative nuclei and moderate to strong cytoplasmic expression (solid arrows). Patient 4 demonstrates negative inflammatory background (empty arrows) tumor cells with variable negative to strong nuclear expression and moderate to strong cytoplasmic positivity (solid arrows). Patient 5 demonstrates negative/weak fibrous stroma (empty arrows) and tumor cells with strong nuclear and cytoplasmic expression (solid arrows). Patient 6 demonstrates negative background lymphocytes/mononuclear inflammatory cells (empty arrows) and tumor cells with strong nuclear and cytoplasmic expression (solid arrows).

Figure 7:
Figure 7:
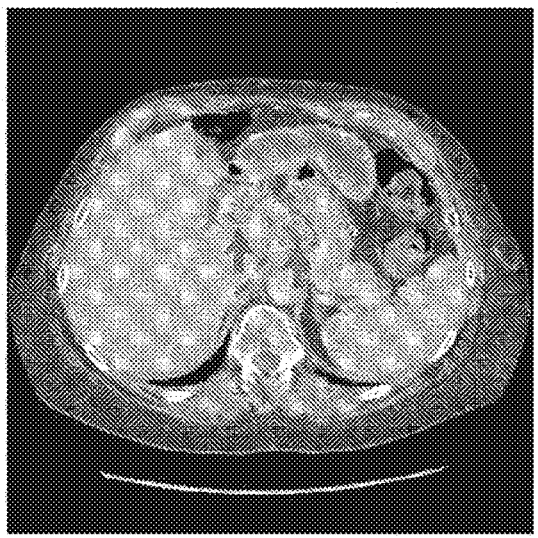
Figure 7:
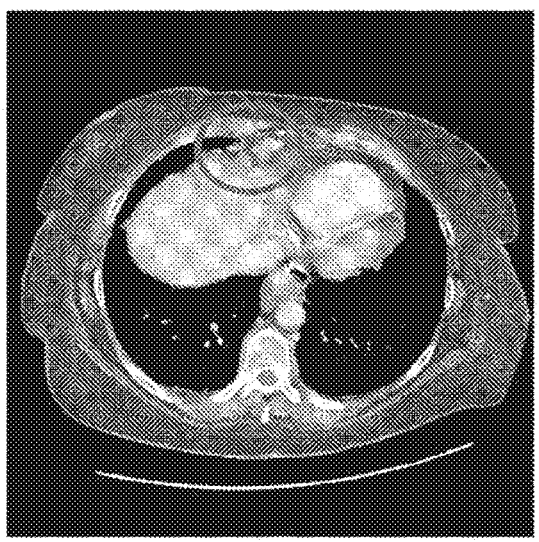
Figure 7:
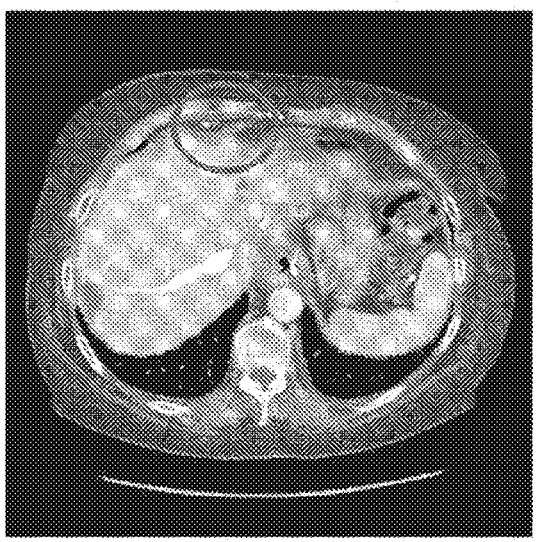

FIG. 7 is an example of anti-tumor activity in Patient 4 harboring an FGFR2-MGEA5 fusion, to FGFR inhibitors. A) CT images of patient 4, whose tumor possessed an FGFR2-MGEA5 fusion, at baseline and 6 weeks demonstrate central necrosis of a caudate liver lobe mass (left arrow), 2.6 cm at baseline and 6 weeks, and shrinkage of a metastatic supraceliac axis lymph node (right arrow), 3.1 cm and 2.9 cm at baseline and 6 weeks respectively. B) CT images of patient 4 showing shrinkage of metastatic lymph nodes involving the right cardiophrenic angle (red circles), 1.3 cm and 0.5 cm at baseline and 6 weeks respectively.

Figure 8:
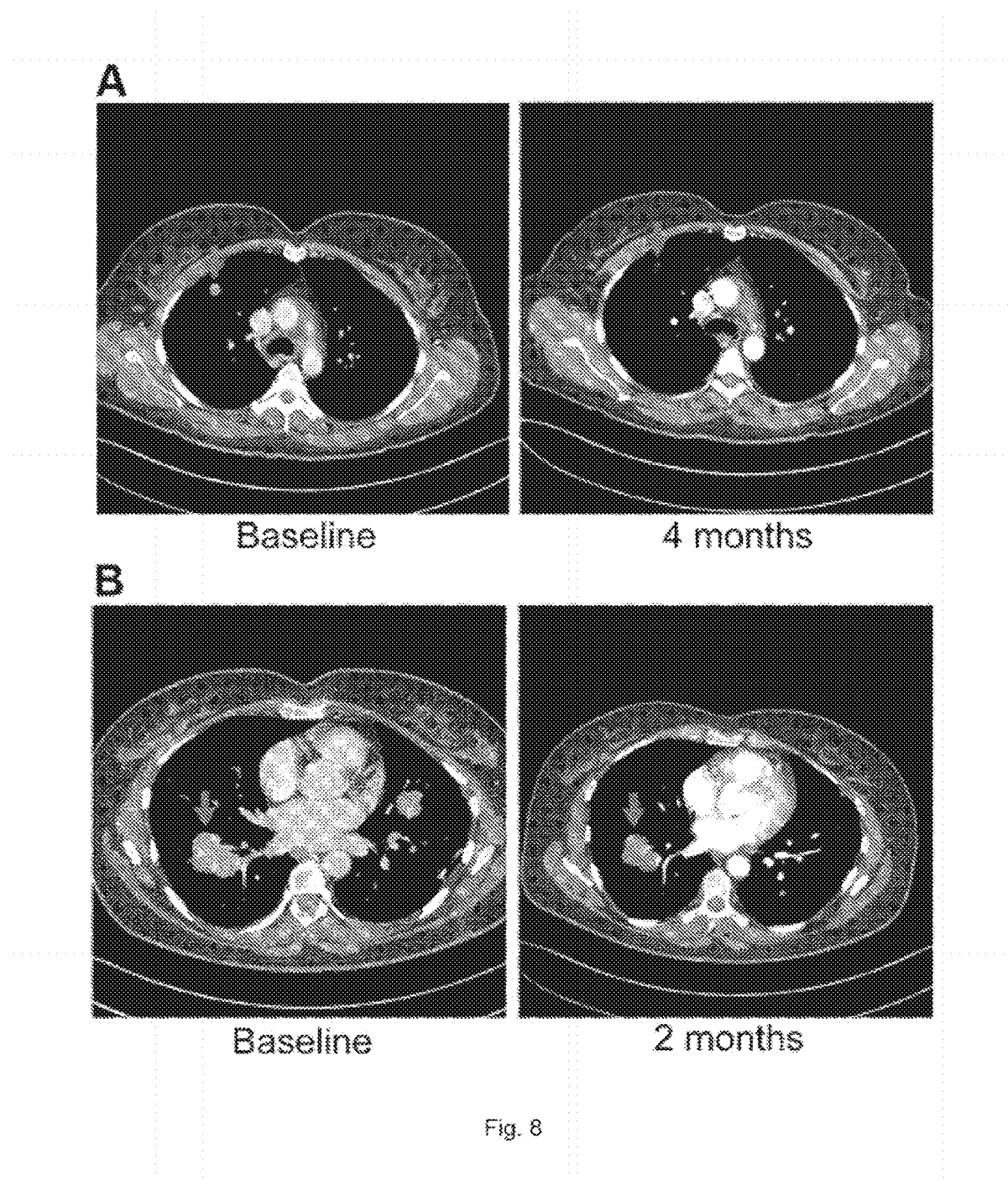

FIG. 8 is an example of anti-tumor activity in Patient 6, harboring an FGFR2-TACC3 fusion, to FGFR inhibitors. A) CT images of patient 6, whose tumor possessed an FGFR2-TACC3 fusion, at baseline and after four months of pazopanib demonstrate significant tumor shrinkage (red arrows), 10.8 mm and 3.1 mm respectively. B) CT images of patient 6 at baseline and two months demonstrate significant tumor shrinkage (red arrows), 41.1 mm and 39.4 mm respectively after subsequent ponatinib treatment, 45 mg/daily, was begun.

Figure 9:
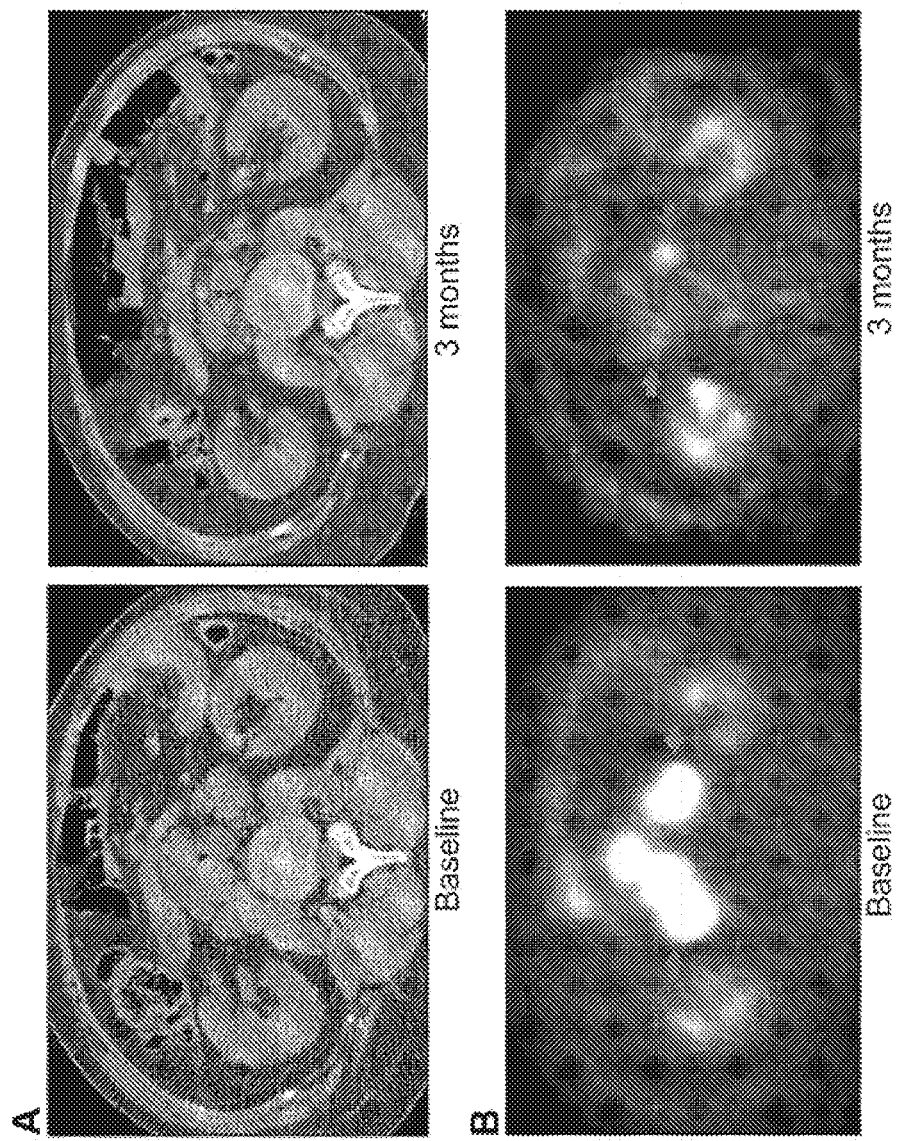

FIG. 9 is an example of anti-tumor activity of Patient 3, harboring an ERRFI1 mutation, to erlotinib, an EGFR inhibitor. A) CT images of patient 3 at baseline and three months demonstrate significant tumor shrinkage (red marks). CT demonstrates right retroperitoneal lymph nodes decreasing from 7.6 cm to 2.9 cm and left retroperitoneal lymph nodes decreasing from 3.3 cm to 1.7 cm. B) PET images of patient 3 at baseline and three months demonstrate significant tumor shrinkage (red arrows). Hypermetabolic areas corresponding to right retroperitoneal lymph nodes demonstrate decrease from 8 cm longest diameter to imperceptible and left retroperitoneal lymph nodes decreasing from 4.2 cm to 1.4 cm. Both regions demonstrated significant reduction in metabolic activity.

Figure 10:
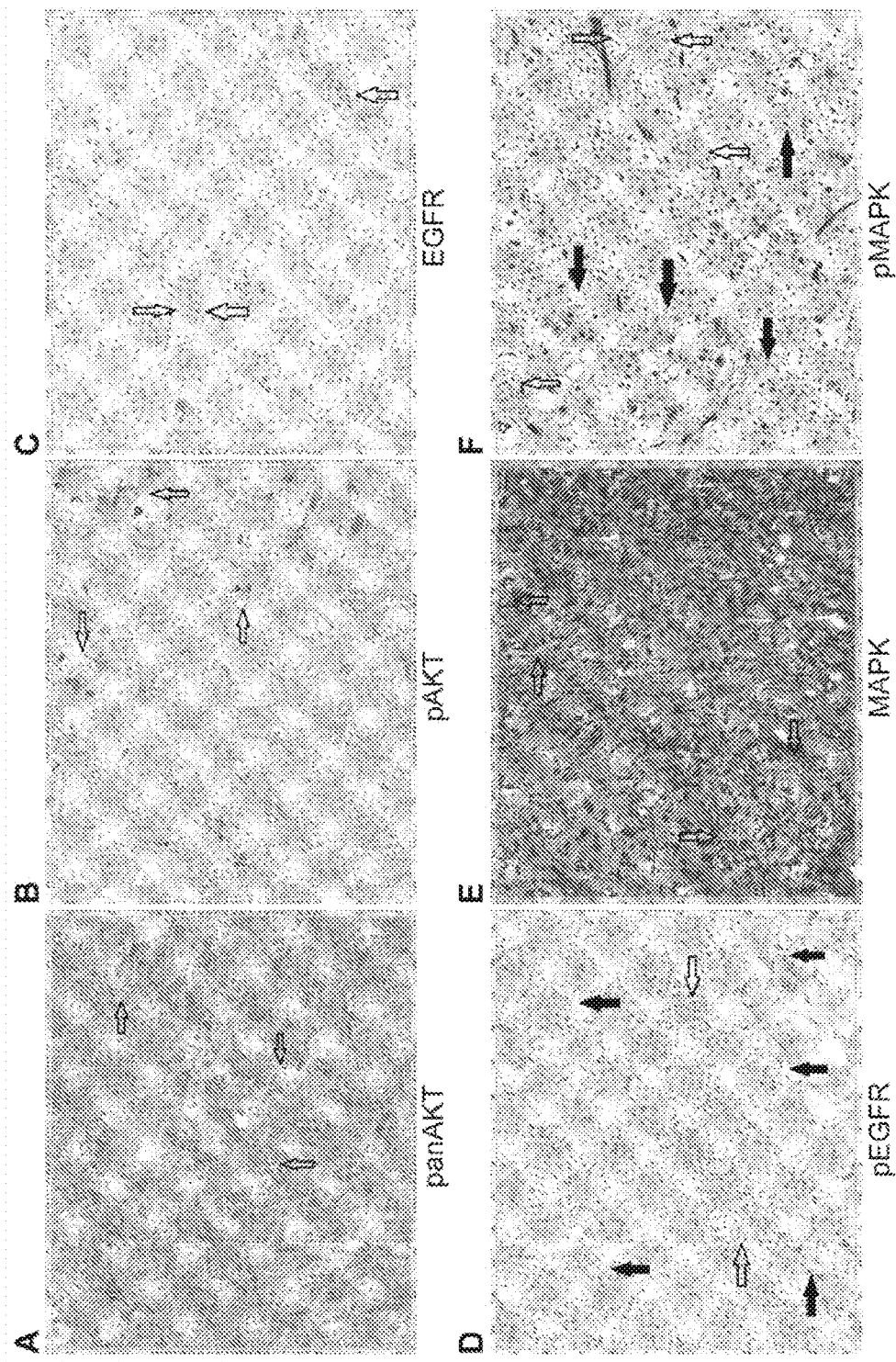

FIG. 10 is depicts immunohistochemistry data of Patient 3's tumor demonstrating activation of the EGFR pathway. A) Tumor stained with panAKT demonstrating diffuse cytoplasmic positivity with negative background lymphocytes (empty arrows). B) Tumor stained with pAKT demonstrating diffuse membranous staining and negative cytoplasmic expression; scattered background inflammatory cells showing strong cytoplasmic staining (empty arrows). C) Tumor stained with EGFR. Tumor cells are EGFR negative with background lymphocytes also negative (empty arrows). D) Tumor stained with pEGFR showing membranous positivity (solid arrows) with negative background lymphocytes (empty arrows). E) Tumor stained with MAPK/ERK1/2 demonstrating moderate to strong cytoplasmic staining of total MAPK with negative background lymphocytes (empty arrows). F) Tumor stained with pMAPK/pERK demonstrating increased expression compared to the negative background lymphocytes (empty arrows).

Figure 11D:
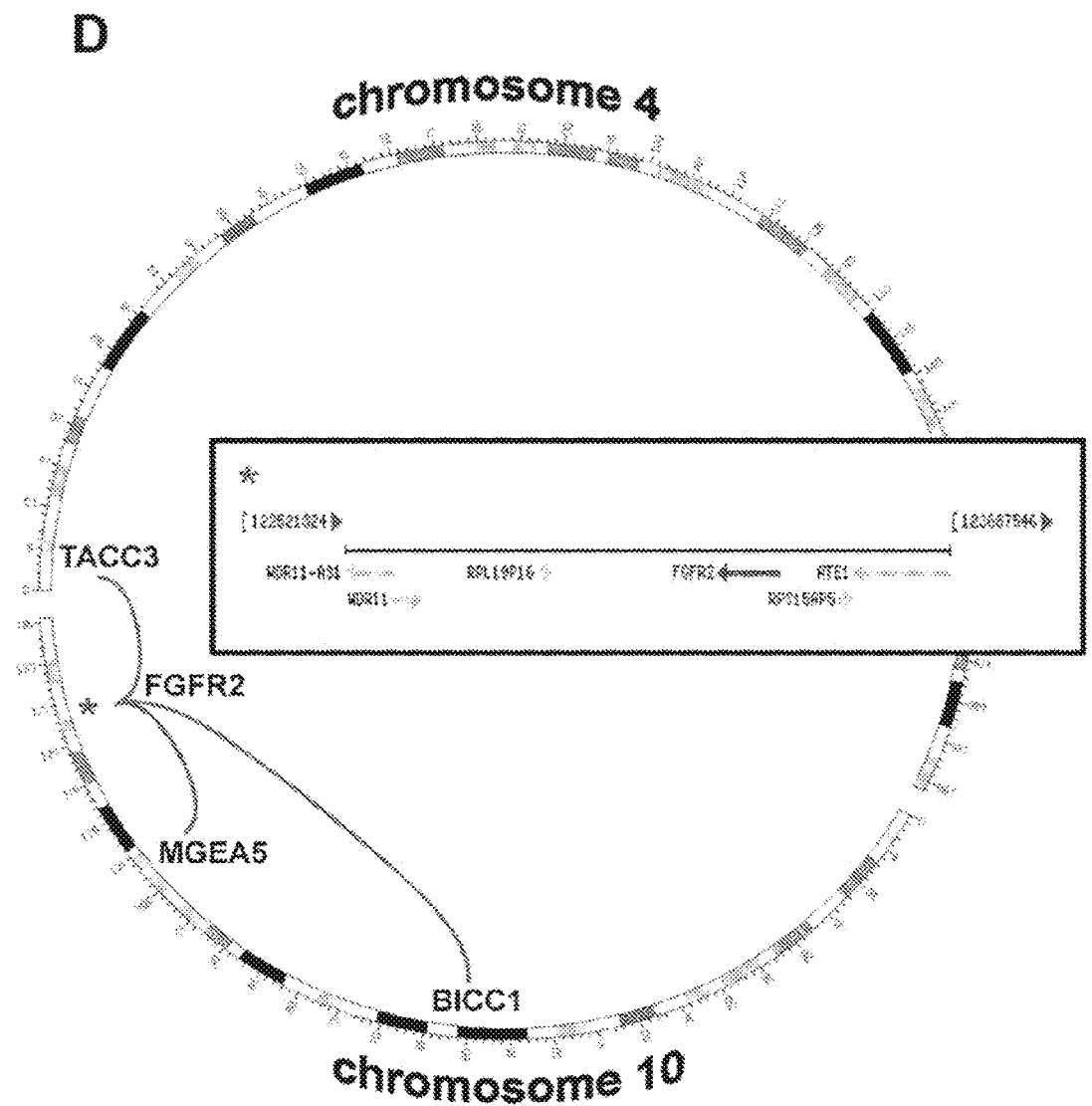

FIG. 11 depict FGFR2-IIIb fusion events. Transcripts and hypothetical protein products are modeled to illustrate the potential functional impact of fusion events involving FGFR2 (A-C). The identified fusion events involving MGEA5 (patient 4) (A) and BICC1 (patient 5, reciprocal event) (C) are chromosome 10 intrachromosomal (D). In addition, patient 6 carried an interchromosomal fusion event (D) involving FGFR2 and TACC3 (B). The FGFR2 gene encodes for several isoforms with eleven representative transcripts and patients 4, 5, and 6 carry fusions involving the epithelial cell specific transcript isoform (FGFR2-IIIb). All identified fusion breakpoints are close in proximity and are predicted to occur within the last intron of the transcript and terminal to a known protein tyrosine kinase domain (A-C, gold domain). Predicted "Other" sites for all of the fusion protein models are the same and include the following: Casein kinase II phosphorylation sites, N-glycosylation sites, Protein kinase C phosphorylation sites, N-myristoylation sites, Tyrosine kinase phosphorylation sites, and cAMP-/cGMP-dependent protein kinase phosphorylation sites (A-C, grey triangle annotations). In all cases, fusions result in a predicted expansion of Casein kinase II phosphorylation and Protein kinase C phosphorylation sites. A protein product model is shown only for one of the reciprocal events involving the FGFR2 and BICC1 genes (FGFR2→BICC1, C). The fusion breakpoints of the reciprocal events effect Exons 1 and 2 of the BICC1 gene, which translates to a difference of a predicted phosphoserine site within the Casein kinase II phosphorylation region (C, purple triangle within red circle). The FGFR2 gene is located within a fragile site region (FRA10F) and is flanked by two ribosomal protein pseudogenes, RPS15AP5 and RPL19P16 (see D inset (*)), whose repetitive sequence content may also contribute to genomic instability at the FGFR2 initiation site.

DETAILED DESCRIPTION OF THE INVENTION

Cholangiocarcinoma is a cancer that affects the bile ducts. Unfortunately, many patients diagnosed with cholangiocarcinoma have disease that cannot be treated with surgery or has spread to other parts of the body, thus severely limiting treatment options. New advances in drug treatment have enabled treatment of these cancers with "targeted therapy" that exploits an error in the normal functioning of a tumor cell, compared to other cells in the body, thus allowing only tumor cells to be killed by the drug.

We sought to identify changes in the genetic material of cholangiocarcinoma patient tumors in order to identify potential errors in cellular functioning by utilizing cutting edge genetic sequencing technology. We identified three patient tumors possessing an FGFR2 gene that was aberrantly fused to another gene. Two of these patients were able to receive targeted therapy for FGFR2 with resulting tumor shrinkage. A fourth tumor contained an error in a gene that controls a very important cellular mechanism in cancer, termed epidermal growth factor pathway (EGFR). This patient received therapy targeting this mechanism and also demonstrated response to treatment. Thus, we have been able to utilize cutting edge technology with targeted drug treatment to personalize medical treatment for cancer in cholangiocarcinoma patients.

Advanced cholangiocarcinoma continues to harbor a difficult prognosis and therapeutic options have been limited. During the course of a clinical trial of whole genomic sequencing seeking druggable targets, we examined six patients with advanced cholangiocarcinoma. Integrated genome-wide and whole transcriptome sequence analyses were performed on tumors from six patients with advanced, sporadic intrahepatic cholangiocarcinoma (SIC) to identify potential therapeutically actionable events. Among the somatic events captured in our analysis, we uncovered two novel therapeutically relevant genomic contexts that when acted upon, resulted in preliminary evidence of anti-tumor activity. Genome-wide structural analysis of sequence data revealed recurrent translocation events involving the FGFR2 locus in three of six assessed patients.

These observations and supporting evidence triggered the use of FGFR inhibitors in these patients. In one example, preliminary anti-tumor activity of pazopanib (in vitro FGFR2 $IC_{50} \approx 350$ nM) was noted in a patient with an FGFR2-TACC3 fusion. After progression on pazopanib, the same patient also had stable disease on ponatinib, a pan-FGFR inhibitor (in vitro, FGFR2 $IC_{50} \approx 8$ nM). In an independent non-FGFR2 translocation patient, exome and transcriptome analysis revealed an allele specific somatic nonsense mutation (E384X) in ERRFI1, a direct negative regulator of EGFR activation. Rapid and robust disease regression was noted in this ERRFI1 inactivated tumor when treated with erlotinib, an EGFR kinase inhibitor. FGFR2 fusions and ERRFI mutations may represent novel targets in sporadic intrahepatic cholangiocarcinoma.

To comprehensively explore the genetic basis of sporadic intrahepatic cholangiocarcinoma (SIC), with emphasis on elucidation of therapeutically relevant targets, we performed integrated whole genome and whole transcriptome analyses on tumors from 6 patients with advanced, sporadic intrahepatic cholangiocarcinoma (SIC). Notably, recurrent fusions involving the oncogene FGFR2 (n=3) were identified. A patient whose tumor presented with an FGFR2-MGEA5 fusion has demonstrated preliminary evidence of anti-tumor activity manifest as stable disease accompanied by CA19-9 reduction and tumor necrosis to ponatinib, a pan-FGFR inhibitor (in vitro FGFR1 $IC_{50} \approx 24$ nM, FGFR2 $IC_{50} \approx 8$ nM, FGFR3 $IC_{50} \approx 8$ nM and FGFR4 $IC_{50} \approx 34$ nM). In another patient whose tumor possessed an FGFR2-TACC3 fusion, preliminary anti-tumor activity of pazopanib (in vitro FGFR2 $IC_{50} \approx 350$ nM) was also noted.

After progression on pazopanib, the same patient also responded to ponatinib and again demonstrated tumor shrinkage. Additionally, a non-FGFR fusion patient was found to have allele-specific preferential expression of a loss of function mutation in ERRFI1, a direct negative regulator of EGFR activation. Similarly, rapid and robust disease regression was noted in the patient with an ERRFI1 mutant tumor when treated with erlotinib, an EGFR kinase inhibitor. Results suggest that these novel targets in the EGFR and FGFR pathways may be therapeutically relevant in patients with sporadic cholangiocarcinoma.

Non-Limiting Examples

Genomic Landscape

Figure 1:
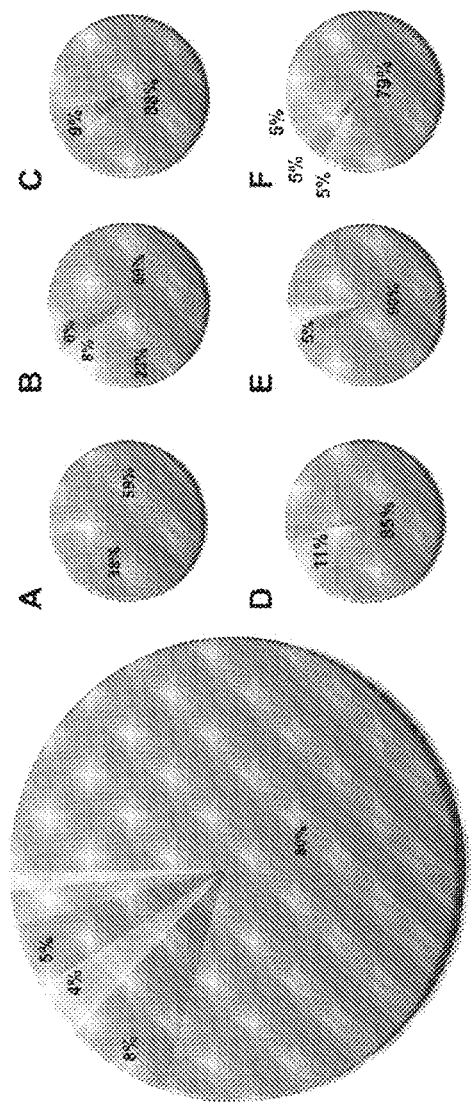
FIG. 1 depicts sequence variation effects. Functional effects of high confidence sequence variations for all of the patients were identified as described in the Methods. The abundance of variations in each functional category is provided as percentages relative to the total number of high confidence variations and raw counts are provided in Table 1. For categories where the percentage was less than 5%, values are not shown. Summaries by individual patients are shown as follows: A) Patient 1, B) Patient 2, C) Patient 3, D) Patient 4, E) Patient 5, and F) Patient 6. Nonsynonymous single nucleotide variations were the predominant class in all of the patients. Two patients, Patients 1 and 2 also accumulated a high number of synonymous mutations in comparison to the other patients; Patient 5 carries the most stops gained likely contributing to a higher number of pseudogenes in comparison to the others; Patient 5 was also the only patient to carry several predicted high impact mutations that affect the splice site acceptor regions (light green, percentage<5%). In addition to the major functional classes summarized, Patient 6 also carried a codon change plus insertion variation.

We identified 327 somatic coding mutations, with an average of 55 mutations/tumor (range 34-112), within our cohort (Table 1, FIG. 1).

TABLE 1

Summary of mutation type by patient.

|  | Patient 1 | Patient 2 | Patient 3 | Patient 4 | Patient 5 | Patient 6 |
| --- | --- | --- | --- | --- | --- | --- |
| Nonsynonymous coding | 20 | 30 | 31 | 44 | 101 | 34 |
| Synonymous coding | 13 | 12 | 0 | 0 | 0 | 0 |
| Insertions/deletions | 1 | 4 | 0 | 6 | 0 | 2 |
| Stop gained | 0 | 3 | 3 | 2 | 6 | 2 |
| Start gained | 0 | 1 | 0 | 0 | 0 | 0 |
| Codon insertion | 0 | 1 | 0 | 0 | 0 | 1 |
| Codon deletion | 0 | 0 | 0 | 0 | 0 | 1 |
| Splice site donor | 0 | 0 | 1 | 0 | 1 | 2 |
| Splice site acceptor | 0 | 0 | 0 | 0 | 4 | 0 |
| Total | 34 | 51 | 35 | 52 | 112 | 42 |

Nonsynonymous single nucleotide variations were the predominant class in all of the patients. Patients 1 and 2 accumulated a high number of synonymous mutations in comparison to the other patients. Patient 5 carried the most stops gained likely contributing to a higher number of pseudogenes in comparison to the others and was also the only patient to carry several predicted high impact mutations affecting splice site acceptor regions (FIG. 1, light green, percentage<5%). In addition, patient 6 also carried a codon change plus insertion variation. Sequencing statistics are provided in Table 2.

TABLE 2

Sequencing metrics of 6 advanced, sporadic biliary tract cancer patients.

| | | Exome | | | | Whole Genome | | | RNA Seq | |
|---|---|---|---|---|---|---|---|---|---|---|
| Patient | Tissue | Aligned Reads (Millions) | Mean Target Coverage | % Target Bases 10x | # of Functional Coding Variants | Aligned Reads (Millions) | Aligned Bases (Billions) | Physical Coverage | Aligned Reads (Millions) | Aligned Bases (Billions) |
| 1 | N | 161 | 100 | 94% | — | 266 | 22 | 37 | — | — |
|   | T | 156 | 112 | 94% | 21 | 228 | 18 | 35 | 100 | 8.1 |
| 2 | N | 176 | 74 | 94% | — | 179 | 14 | 5 | — | — |
|   | T | 202 | 81 | 94% | 34 | 370 | 30 | 10 | 341 | 26 |
| 3 | N | 226 | 110 | 58% | — | 296 | 24 | 50 | 163 | 13 |
|   | T | 195 | 92 | 58% | 52 | 321 | 26 | 50 | 101 | 8.1 |
| 4 | N | 167 | 80 | 95% | — | 317 | 26 | 42 | — | — |
|   | T | 202 | 93 | 96% | 52 | 163 | 13 | 12 | 264 | 20 |
| 5 | N | 257 | 146 | 96% | — | 335 | 27 | 51 | — | — |
|   | T | 133 | 78 | 93% | 250 | 349 | 28 | 39 | 401 | 31 |
| 6 | N | 350 | 243 | 92% | — | — | — | — | — | — |
|   | T | 340 | 245 | 92% | 43 | — | — | — | 713 | 31 |
| Liver Control | — | — | — | — | — | — | — | — | 118 | 9.6 |

N = Normal,
T = Tumor.

Genes with mutations in more than one case included CSPG4 (n=2), GRIN3A (n=2) and PLXBN3 (n=2). While there was overlap in the somatic landscape of SIC with liver-fluke associated cholangiocarcinoma, hepatocellular cancer and pancreatic cancer, most of the aberrations detected in our study were distinct (Table 3).

TABLE 3

Comparison of mutation frequency in cholangiocarcinoma, pancreatic and liver cancers.

| Gene | Non-liver fluke CCA (n = 6) | Liver fluke associated CCA (n = 54) | CCA (n = 62) | PDAC (n = 142) | HCC (n = 149) |
|---|---|---|---|---|---|
| AKT1 | 0% | 0% | 1.6% | 0% | 0% |
| APC | 0% | 0% | 0% | 0% | 1.3% |
| ARID2 | 0% | 0% | NA | 2.1% | 6.0% |
| BAP1 | 16.7% | 0% | NA | 0% | 0% |
| BRAF | 0% | 0% | 1.6% | 0.7% | 0% |
| CDKN2A | 0% | 5.6% | NA | 2.4% | 7.4% |
| CSPG4 | 33.3% | 0% | NA | 0% | 0.7% |
| CTNNB1 | 0% | 0% | NA | 0% | 34.9% |
| DMXL1 | 0% | 0% | NA | 0% | 0% |
| EGFR | 0% | 0% | 0% | 0% | 0% |
| ERRFI1 | 16.7% | 0% | NA | 0% | 0.7% |
| FLT3 | 0% | 0% | 0% | 0% | 0% |
| GNAS | 0% | 9.3% | NA | 0.7% | 0% |
| GRIN3A | 33.3% | 0% | NA | 0% | 0% |
| IDH1 | 0% | 0% | 13% | 0% | 0% |
| IDH2 | 16.7% | 0% | 2% | 0% | 0% |
| JAK2 | 0% | 0% | 0% | 0% | 0% |
| KIT | 0% | 0% | 0% | 0% | 0% |
| KRAS | 0% | 16.7% | NA | 66.2% | 1.3% |
| LAMA2 | 16.7% | 3.7% | NA | 0% | 0% |
| MLL3 | 16.7% | 14.8% | NA | 4.9% | 0% |
| NDC80 | 0% | 3.7% | NA | 0% | 0% |
| NLRP1 | 16.7% | 0% | NA | 0% | 0% |
| NOTCH1 | 16.7% | 0% | 0% | 0% | 0% |
| NRAS | 16.7% | 0% | 3.2% | 0% | 0% |
| PCDHA13 | 16.7% | 3.7% | NA | 0.7% | 0% |
| PAK1 | 16.7% | 0% | NA | 0% | 0% |
| PEG3 | 0% | 5.6% | NA | 1.4% | 0% |
| PIK3CA | 0% | 0% | 0% | 0% | 1.3% |
| PLXNB3 | 33.3% | 0% | NA | 0% | 0% |
| PTEN | 0% | 3.7% | 2% | 0% | 0% |
| PTK2 | 16.7% | 0% | NA | 0% | 0% |
| RADIL | 0% | 3.7% | NA | 0% | 0% |
| RNF43 | 0% | 9.3% | NA | 0% | 0% |
| ROBO2 | 0% | 9.3% | NA | 1.4% | 0% |
| SMAD4 | 0% | 16.7% | NA | 11.3% | 0% |
| TP53 | 33.3% | 44.4% | 8% | 23.2% | 19.5% |
| XIRP2 | 0% | 5.6% | NA | 3.5% | 0% |

CCA, cholangiocarcinoma; PDAC, pancreatic ductal adenocarcinoma; HCC, hepatocellular carcinoma; NA, not assessed.

Figure 2:
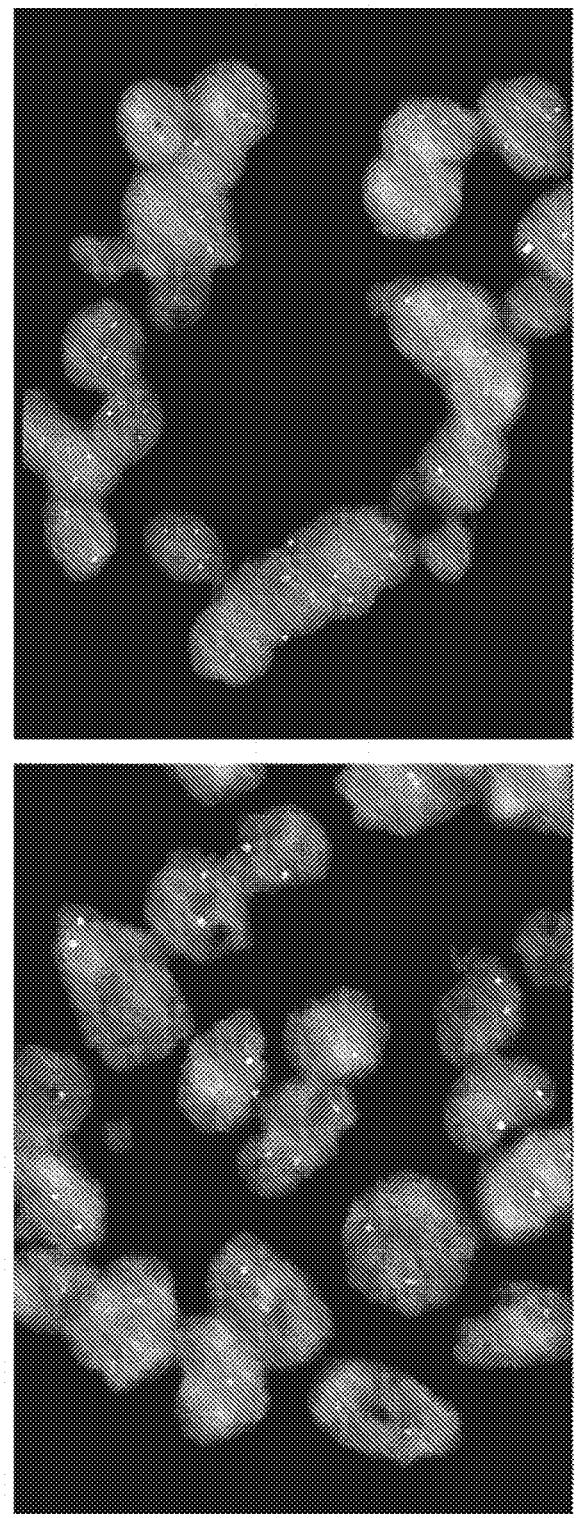
FIG. 2 depicts representative fluorescent in situ hybridization (FISH) demonstrating the presence of FGFR2 fusion. A) Cholangiocarcinoma with FGFR2 rearrangement (distinct orange and green signals are present in most of the cells). B) Cholangiocarcinoma negative for FGFR2 rearrangement (orange and green signals remain fused).

More importantly, using previously published methods [21], we identified molecular fusions involving FGFR2 that were felt to be therapeutically relevant in 3 patients. Additionally, these fusions were validated with a break apart Fluorescent In situ Hybridization (FISH) assay (FIG. 2).

Notably, the patients who did not harbor the FGFR2 fusions were negative using the same assay. Two of the three patients with FGFR2 fusions (Patients 4 and 6) were treated with FGFR inhibitors while the third patient (Patient 5), experienced clinical decline prior to the availability of results and as such did not receive any further therapy. Furthermore, overexpression of an SNV in ERRFI1 (E384X), a negative regulator of EGFR, was detected in a non-FGFR2 translocation patient's tumor. Taken together, our results constitute important therapeutically actionable alterations in patients with advanced SIC.

Comparison of Mutation Frequency in Cholangiocarcinoma, Pancreatic and Liver Cancers.

Pathway Analysis

Figure 3A:
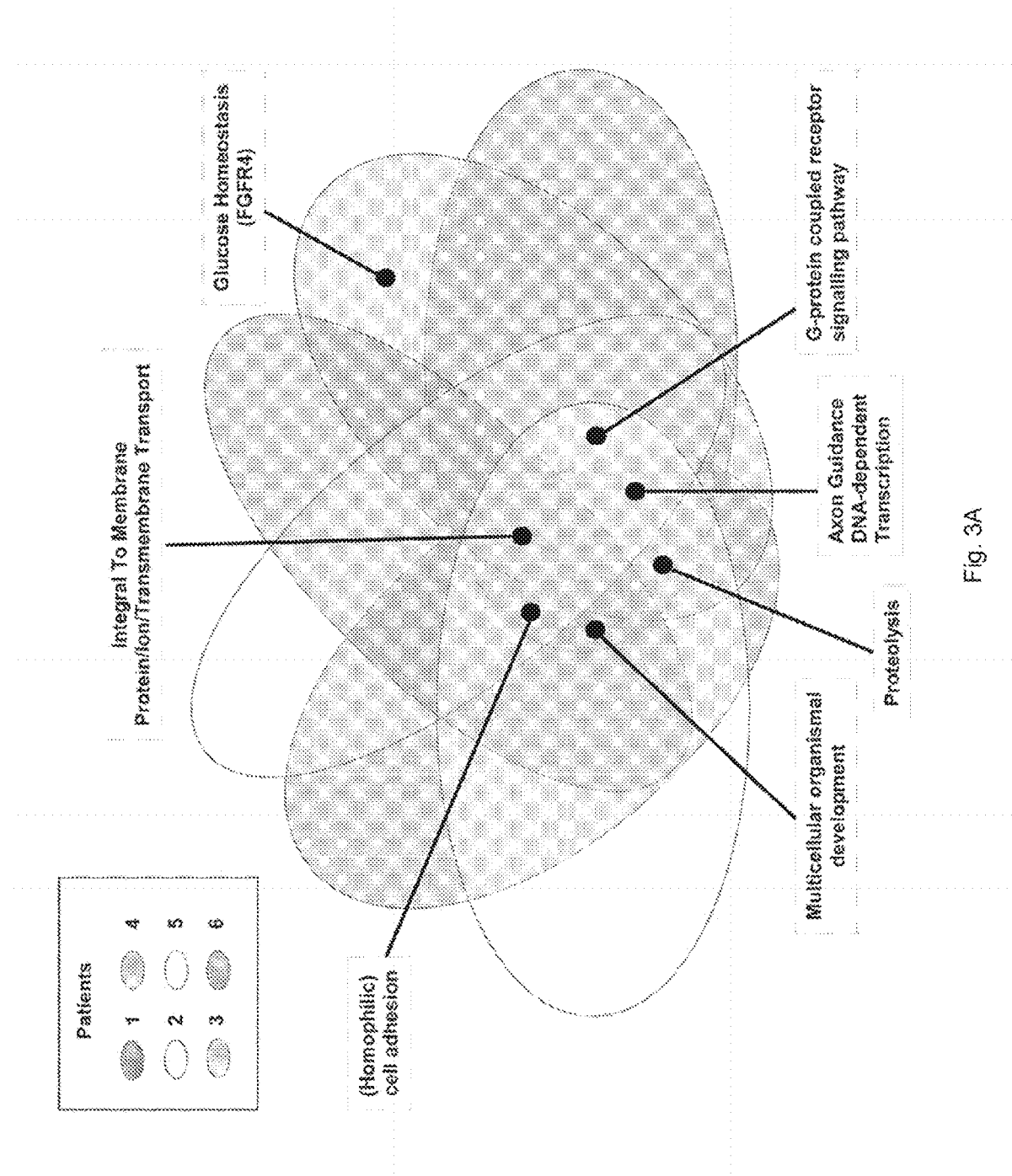
FIG. 3 depicts a gene ontology pathway analysis. Genes carrying single nucleotide or frameshift variations, or aberrant in copy number were annotated and clustered by GO term functional classes, some of which are known to play a role in cancer. Major classes for A) SNVs and B) CNVs are labeled in the figure. Proteins predicted to be integral to the membrane and involved in transport, as well as transcriptional regulators were among the most abundant class in all of the patients affected by small scale sequence variations and copy number variations. Variations specifically affecting the EGFR or FGFR gene families were prevalent in Patients 4, 5, and 6 and are highlighted in the figure with the gene name provided in parenthesis next to the pathway name.
Figure 3B:
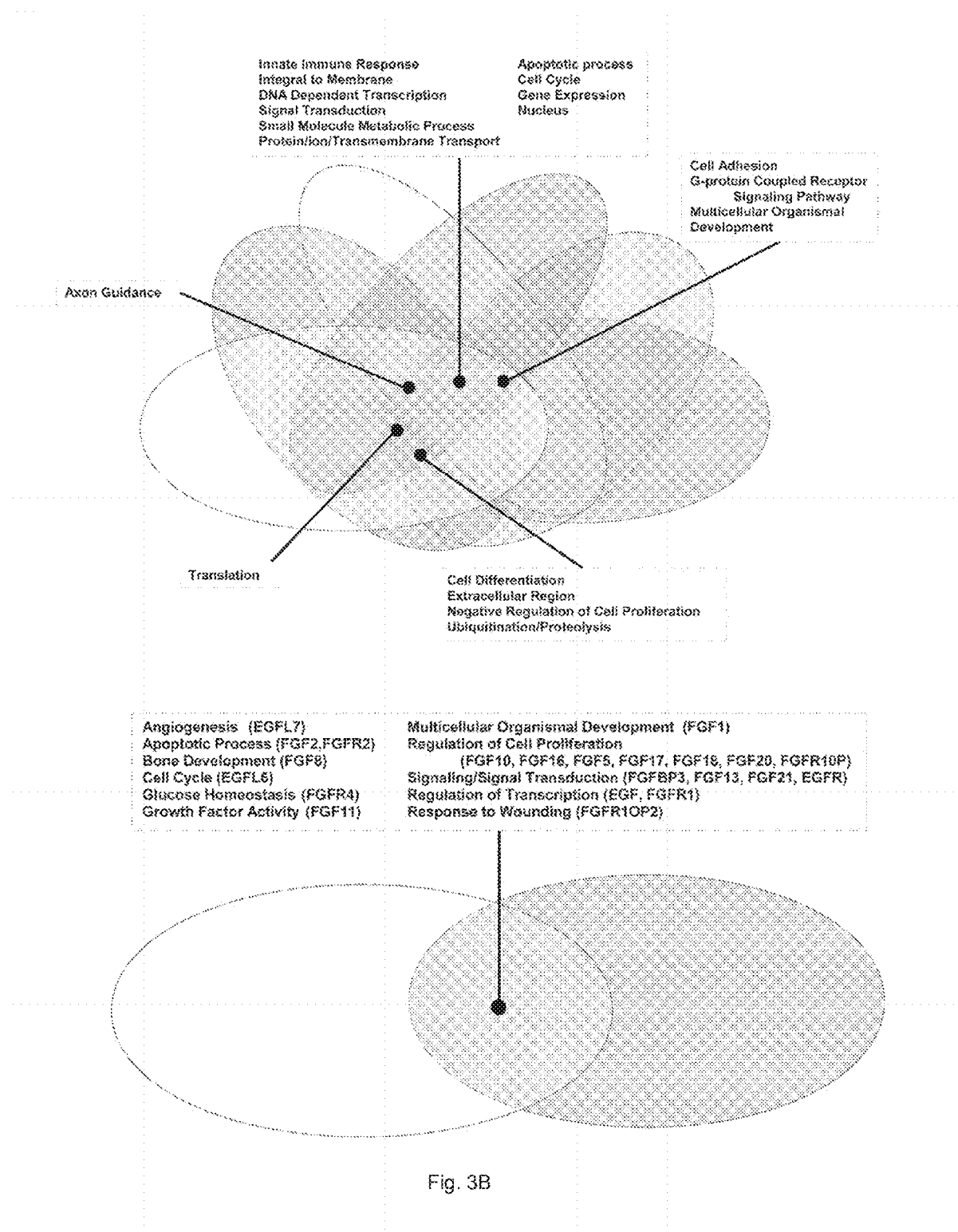

Comparative pathway analysis of genes carrying small scale nucleotide variations (SsNVs) has implicated several major pathways, possibly interacting as a network, that are predicted to underlie disease in all of our studied biliary carcinoma patients. These shared pathways include EGFR, EPHB, PDGFR-beta, Netrin-mediated and Beta1 integrin mediated signaling pathways (FIG. 3). Interestingly, most of these pathways have known roles in mediating epithelial-to-mesenchymal cell transitions, which occur frequently during development as well as tumorigenesis. Cell growth and motility is inherent to the successful progression of both biological processes. Studies of the nervous system and lung development have shown that Netrins act to inhibit FGF7 and FGF10 mediated growth or cell guidance.

Patients 3 and 4 also shared several genes acting in cadherin signaling pathways which are important for maintaining cell-cell adhesion and are known to be intimately integrated with EGFR and FGFR signaling pathways.

Gene Ontology Pathway Analysis.

In addition to the variations identified in genes acting in EGFR and/or FGFR signaling pathways, we also report multiple sSNVs and copy number variations (CNVs) (FIG. 4) in genes such as HDAC1, TP53, MDM2 and AKT1, acting in interaction networks or regulatory pathways involving the fusion partner genes in patients 5 (BICC1), and 6 (TACC3) (Table 4).

Known mutations in BICC1 have been shown to disrupt canonical Wnt signaling and genes, such as BCL9, involved in this pathway are known to regulate a range of biological processes such as transcription and cell proliferation and carry variations in patient 5 (Table 4). CSPG4, a target that is being investigated for antibody-based immunotherapy in preclinical studies of triple negative breast cancer, is involved in the Wnt signaling pathway, and carries variations in both patients 1 and 2, however, it is not mutated in patient 5. TACC3 is known to mediate central spindle assembly and multiple genes including CDCA8, BUB1, and TACC1, belonging to the TACC3 interaction network exhibit aberrant copy number in patient 6 (Table 4). A recent study has also implicated TACC3 in EGF-mediated EMT when overexpressed and we find that the PLCG1, MAP2K1, and MAPK8 genes, which act in both FGFR and EGFR regulatory pathways, exhibit CNV in patient 6. We also note that the DNAH5 gene encoding a dynein protein which is part of the microtubule-associated motor protein complex carries two G→C missense mutations in patient 6.

Several genes carrying more than one variation in either the same patient or different patients also included genes with known roles similar to genes in FGFR/EGFR pathways including axon guidance, invasive growth, or cell differentiation (NAV3, LAMC3, PLXNB3, and PTPRK). In the case of patient 4, our studies suggest that the primary effect of the FGFR2-MGEA5 fusion is on FGFR2 related signaling, since changes in expression were observed in FGF8 ($p<0.05$) and the genome of this patient also carries a 4-bp insertion (AGTGT) in the FGFR4 gene.

TABLE 4

Stable fusion partner gene pathways.

| Patients | Gene in Interaction or Regulatory Network | Small-scale Variation (sSNV)/Copy Number Variation (CNV) | Associated Network | Associated Pathway |
|---|---|---|---|---|
| 4 | FGFR4 | ssNV | FGFR | glucose homeostasis |
| 5 | RAF1 | CNV | EGFR/FGFR | axon guidance |
| 5 | RPS6KA5 | CNV | FGFR | innate immune response |
| 5 | HGF | CNV | FGFR | mitosis |
| 5 | FRS2 | CNV | FGFR | ventricular septum development |
| 5 | FGFR2 | CNV | FGFR | apoptotic process |
| 5 | FGFR4 | CNV | FGFR | glucose homeostasis |
| 5 | FGFR1OP2 | CNV | FGFR | response to wounding |
| 5 | FGFR1 | CNV | FGFR | transcription, DNA-dependent |
| 5 | ANTXR1 | CNV | BICC1 | actin cytoskeleton reorganization |
| 5 | ARL3 | CNV | BICC1 | cell cycle |
| 5 | NKX3-1 | CNV | BICC1 | multicellular organismal development |
| 5 | WIF1 | CNV | BICC1 | multicellular organismal development |
| 5 | AXIN2 | CNV | BICC1 | negative regulation of cell proliferation |
| 5 | SFRP1 | CNV | BICC1 | negative regulation of cell proliferation |
| 5 | HDAC1 | CNV | BICC1 | negative regulation of transcription from RNA polymerase II promoter |
| 5 | HNF1A | CNV | BICC1 | positive regulation of transcription, DNA-dependent |
| 5 | NR5A2 | CNV | BICC1 | positive regulation of transcription, DNA-dependent |
| 5 | IPO13 | CNV | BICC1 | protein import into nucleus |
| 5 | MAP3K7 | CNV | BICC1 | transcription, DNA-dependent |
| 5 | SLC6A20 | CNV | BICC1 | transmembrane transport |
| 5 | BTRC | CNV | BICC1 | ubiquitin-dependent protein catabolic process |
| 5 | BCL9 | CNV | BICC1 | Wnt receptor signaling pathway |
| 5 | TP53 | ssNV | BICC1 | transcription, DNA-dependent |
| 6 | PLCG1 | CNV | EGFR/FGFR | axon guidance |
| 6 | MAP2K1 | CNV | EGFR/FGFR | innate immune response |
| 6 | MAPK8 | CNV | EGFR/FGFR | peptidyl-threonine phosphorylation |
| 6 | GAB1 | CNV | FGFR | heart development |
| 6 | ATF2 | CNV | FGFR | innate immune response |
| 6 | MAPKAPK2 | CNV | FGFR | innate immune response |
| 6 | RPS6KA5 | CNV | FGFR | innate immune response |
| 6 | HGF | CNV | FGFR | mitosis |
| 6 | FRS2 | CNV | FGFR | ventricular septum development |
| 6 | FGF2 | CNV | FGFR | apoptotic process |

TABLE 4-continued

Stable fusion partner gene pathways.

| Patients | Gene in Interaction or Regulatory Network | Small-scale Variation (sSNV)/Copy Number Variation (CNV) | Associated Network | Associated Pathway |
|---|---|---|---|---|
| 6 | FGFR2 | CNV | FGFR | apoptotic process |
| 6 | FGFR4 | CNV | FGFR | glucose homeostasis |
| 6 | FGF17 | CNV | FGFR | positive regulation of cell proliferation |
| 6 | FGF18 | CNV | FGFR | positive regulation of cell proliferation |
| 6 | FGF20 | CNV | FGFR | positive regulation of cell proliferation |
| 6 | FGFR1OP | CNV | FGFR | positive regulation of cell proliferation |
| 6 | FGFR1 | CNV | FGFR | transcription, DNA-dependent |
| 6 | MDM2 | CNV | TACC3 | protein ubiquitination |
| 6 | E2F2 | CNV | TACC3 | apoptotic process |
| 6 | GADD45A | CNV | TACC3 | apoptotic process |
| 6 | HMGB2 | CNV | TACC3 | apoptotic process |
| 6 | RHOA | CNV | TACC3 | axon guidance |
| 6 | PEBP1 | CNV | TACC3 | brain development |
| 6 | EVI5 | CNV | TACC3 | cell cycle |
| 6 | CDCA8 | CNV | TACC3 | cell division |
| 6 | CKAP5 | CNV | TACC3 | cell division |
| 6 | PPP1CC | CNV | TACC3 | cell division |
| 6 | BUB1 | CNV | TACC3 | cell proliferation |
| 6 | GTSE1 | CNV | TACC3 | DNA damage response, signal transduction by p53 class mediator resulting in cell cycle arrest |
| 6 | TACC1 | CNV | TACC3 | microtubule cytoskeleton organization |
| 6 | KIF20A | CNV | TACC3 | microtubule-based movement |
| 6 | KIF2C | CNV | TACC3 | microtubule-based movement |
| 6 | NCAPH | CNV | TACC3 | mitosis |
| 6 | NSUN2 | CNV | TACC3 | mitosis |
| 6 | AKAP9 | CNV | TACC3 | mitotic cell cycle |
| 6 | KIF23 | CNV | TACC3 | mitotic cell cycle |
| 6 | MCM5 | CNV | TACC3 | mitotic cell cycle |
| 6 | NPM1 | CNV | TACC3 | negative regulation of cell proliferation |
| 6 | CBX5 | CNV | TACC3 | negative regulation of transcription, DNA-dependent |
| 6 | MKI67 | CNV | TACC3 | organ regeneration |
| 6 | AURKAIP1 | CNV | TACC3 | positive regulation of proteolysis |
| 6 | AKT1 | CNV | TACC3 | protein ubiquitination |
| 6 | BRCA1 | CNV | TACC3 | protein ubiquitination |
| 6 | KLHL13 | CNV | TACC3 | protein ubiquitination |
| 6 | KLHL9 | CNV | TACC3 | protein ubiquitination |
| 6 | TTF2 | CNV | TACC3 | regulation of transcription, DNA-dependent |
| 6 | RACGAP1 | CNV | TACC3 | signal transduction |
| 6 | TDRD7 | CNV | TACC3 | spermatogenesis |
| 6 | PRKACA | CNV | TACC3 | transmembrane transport |

FGFR2-MGEA5 as a Putative Therapeutic Target

Patient 4 is a 62 year-old white female found to have a left-sided intrahepatic mass with satellite lesions, with metastasis to regional lymph nodes (Table 5).

TABLE 5

Clinical characteristics of 6 advanced, sporadic biliary tract cancer patients.

| | Patient 1 | Patient 2 | Patient 3 | Patient 4 | Patient 5 | Patient 6 |
|---|---|---|---|---|---|---|
| Age (years) | 64 | 66 | 50 | 62 | 50 | 43 |
| Gender | F | M | M | F | F | F |
| Location of Primary Tumor | Intrahepatic | Intrahepatic/Gallbladder | Intrahepatic | Intrahepatic | Intrahepatic | Intrahepatic |
| Stage | III | IV | IV | IV | IV | IV |
| CA19-9 (Units/ml) | WNL | 1008 | WNL | WNL* | N/A | 56 |
| Sites of Metastasis | N/A | Abdominal Lymph Nodes | Cervical, Thoracic, Abdominal, Pelvic Lymph Nodes | Abdominal, Pelvic Lymph Nodes, Liver | Liver, Lungs, Peritoneum | Lungs |
| Underlying Etiology | Unknown | Unknown | Unknown | Unknown | Unknown | Unknown |
| Liver fluke | No | No | No | No | No | No |
| Hepatitis B | Unknown | Unknown | Negative | Unknown | Unknown | Unknown |
| Hepatitis C | Unknown | Unknown | Negative | Unknown | Unknown | Unknown |
| Prior Surgical Resection | No | Yes | Yes | No | Yes | No |
| Prior Radiation Therapy | No | No | No | No | No | No |
| Systemic Chemotherapy | Gem/Cis | Gem/Cis, Capecitabine | Gem/Cis | Gem/Cis, Gem/Cape, PEGPH20 | Gem/Cis, 5-FU/Carbo | Gem/Cis, FOLFOX, Pazopanib |
| Survival Status | Alive | Dead | Dead | Alive | Dead | Alive |

TABLE 5-continued

Clinical characteristics of 6 advanced, sporadic biliary tract cancer patients.

|  | Patient 1 | Patient 2 | Patient 3 | Patient 4 | Patient 5 | Patient 6 |
|---|---|---|---|---|---|---|
| Survival Duration from biopsy (months) | 14.5+ | 8.8 | 9.0 | 9.3+ | 4.1 | 5.5+ |

F = female;
M = male;
WNL = Within Normal Limits;
Gem/Cis = Gemcitabine and Cisplatin;
Gem/Cape = Gemcitabine and Capecitabine;
PEGPH20 = pegylated hyaluronidase;
5-FU/Carbo = 5-Fluorouracil and Carboplatin;
FOLFOX - 5-FU, Leucovorin and Oxaliplatin,
*= WNL at baseline but 1408 U/ml prior to therapy and N/A = Not Available.

A biopsy of the liver mass revealed the presence of a poorly differentiated adenocarcinoma that was consistent with intrahepatic cholangiocarcinoma (CK7$^+$, CEA$^+$, CK20$^+$, Hep-par 1$^-$, TTF-1$^-$) (Table 6).

TABLE 6

Pathological characteristics of 6 advanced, sporadic biliary tract cancer patients.

|  | Patient 1 | Patient 2 | Patient 3 | Patient 4 | Patient 5 | Patient 6 |
|---|---|---|---|---|---|---|
| Grade/differentiation | Moderate | Moderate | Undifferentiated** | Poor | Moderate | Poor |
| Biopsy Procedure | U/S Guided Liver Biopsy | U/S Guided Liver Biopsy | Excisional Biopsy Lymph Node | U/S Guided Liver Biopsy | U/S Guided Liver Biopsy | Excisional Lung Biopsy |
| % Necrosis (aliquots) | 5 (1) | 0 (2) | 0-35 (7) | 0 (3) | 0-5 (3) | 0 |
| % Tumor | 50 | 10-20 | 25-75 | 0-20 | 40-50 | 30 |
| % Stroma and normal elements | 50 | 80-90 | 25-75 | 80-100 | 50-60 | 70 |
| Histological Type | NST* | NST | NST | NST | NST | NST |
| Clear Cell Histology (Yes/No) | No | No | No | No | No | No |

U/S = Ultrasound.
*NST: No special type.
**Rare gland formation with expression of cytokeratin, polyclonal CEA, and MOC-31.

All were adenocarcinomas of no special types and high grades as defined by the World Health Organization Classification of Tumors of the Digestive System. Degree of differentiation is based on the percentage of glands (defined as having visible lumens by visual estimate) as follow: 95% or more glands-well differentiated, 40-94% glands-moderately differentiated, 5-39% glands-poorly differentiated, <5% glands-undifferentiated.

Figure 5:
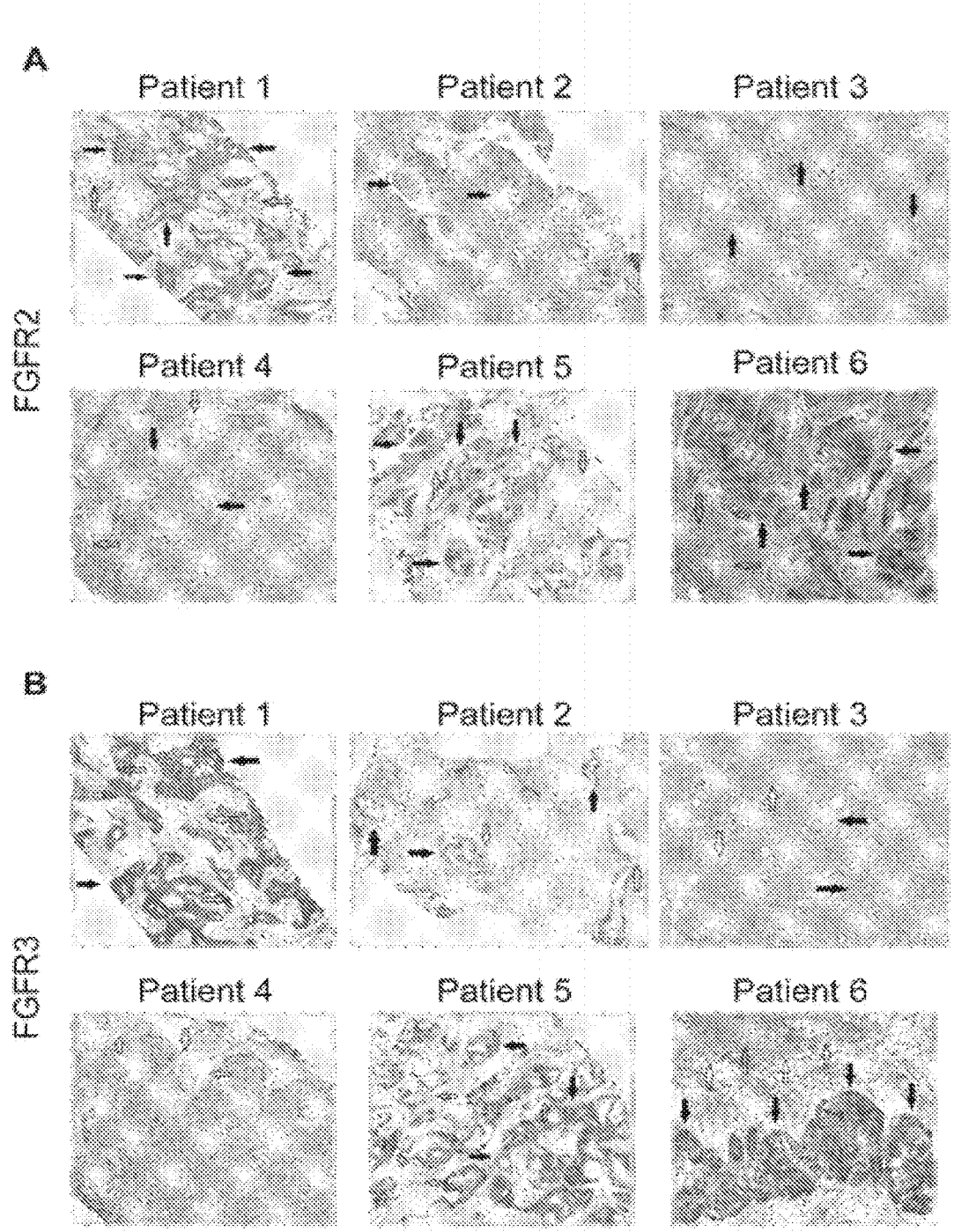
FIG. 5 depicts immunohistochemistry data demonstrating FGFR2 and FGFR3 expression. A) Tumor stained with FGFR2 antibody. Patient 1 demonstrates moderate cytoplasmic positivity (solid arrows); background fibro-inflammatory tissue is negative (empty arrows). Patient 2 demonstrates moderate cytoplasmic expression for FGFR2; tumor nuclei are negative. Patient 3 demonstrates tumor cells with negative nuclear and weak cytoplasmic expression of FGFR2 (solid arrows) with cells demonstrating moderate basolateral or complete membranous staining as well. Patient 4 demonstrates weak/moderate cytoplasmic positivity with multi-focal weak/moderate membranous expression (solid arrows); background fibro-inflammatory tissue demonstrates negative/weak staining (empty arrows). Patient 5 demonstrates weak/moderate cytoplasmic positivity with multi-focal moderate/strong membranous expression (solid arrows); background fibro-inflammatory tissue is negative (empty arrows). Patient 6 demonstrates moderate/strong cytoplasmic positivity (solid arrows); background lymphocytes are negative (empty arrows). B) Tumor stained with FGFR3 antibody. Patient 1 demonstrates strong cytoplasmic positivity, variable nuclear expression and occasional moderate/strong membranous expression (solid arrows); background fibrous tissue is negative (empty arrows). Patient 2 demonstrates negatively staining background neutrophils (focally intraepithelial-far right) (empty arrows) and tumor cells with strong nuclear expression and moderate cytoplasmic positivity (solid arrows). Patient 3 demonstrates negatively staining background inflammation (empty arrows) and tumor cells with weak nuclear expression and moderate cytoplasmic positivity (solid arrows). Patient 4 demonstrates weak/moderate cytoplasmic positivity and variable nuclear expression; background fibro-inflammatory tissue demonstrates negative/weak positivity (empty arrows). Patient 5 demonstrates moderate cytoplasmic positivity, variable nuclear expression and strong multi-focal membranous expression (solid arrows); background fibrous tissue is negative. Patient 6 demonstrates diffuse/moderate/strong cytoplasmic and membranous positivity and variable nuclear expression (solid arrows); background lymphocytes are negative (empty arrows).

She received gemcitabine and cisplatin and obtained clinical benefit in the form of stable disease for 6 months, followed by disease progression. She was re-treated with gemcitabine and capecitabine systemic therapy and attained stable disease for 6 months, followed by disease progression. A clinical trial of pegylated hyaluronidase (PEGPH20) produced only stable disease for 4 months, followed again by disease progression. At this juncture, she underwent a liver biopsy to obtain tissue for whole genome characterization of her tumor. She was found to have an FGFR2-MGEA5 fusion (Table 7, FIG. 2) and ponatinib monotherapy was pursued as salvage treatment. Evaluation of pre-treatment immunohistochemistry demonstrated increased expression of FGFR2 and FGFR3 (FIG. 5) and Clinical Laboratory Improvement Amendments (CLIA) validation by quantitative PCR revealed increased expression of FGFR3. In order to further validate the activation of the receptor, we conducted immunohistochemistry (IHC) of pFRS2 Y436 and pERK(MAPK) that revealed strong expression of pFRS2 Y436 and pERK (FIG. 6), thus confirming activation of the receptor.

TABLE 7

Fusion events.

|  | Gene1 | Gene2 | Gene1 break location | Gene2 break location | Predicted Reciprocal Translocation | Patient |
|---|---|---|---|---|---|---|
| Fusions | FGFR2 | MGEA5 | chr10: 123243211 | chr10: 103552699 | No | 4 |
|  | FGFR2 | BICC1 | chr10: 123237843 | chr10: 60380614 | Yes | 5 |
|  | BICC1 | FGFR2 | chr10: 60272900 | chr10: 123237848 | Yes | 5 |
|  | FGFR2 | TACC3 | chr10: 123243211 | chr4: 1741428 | No | 6 |

Fusion Events.

Ponatinib was initiated at 45 mg given orally on a daily schedule. Approximately 6 weeks after initiation of therapy she was noted to have anti-tumor activity that was characterized by central necrosis of a caudate liver lobe mass, shrinkage of metastatic lymph nodes involving the right cardiophrenic angle, central necrosis and shrinkage of a metastatic supraceliac axis lymph node (FIG. 7) and reduction in CA 19-9 from 1408 Um' to 142 U/ml. Per RECIST criteria, she exhibited stable disease with a 14% decrease in the sum of largest diameters but with tumor necrosis and reduction in the CA19-9 tumor marker (89.8%). While the evidence is preliminary in nature, it was felt that the combination of tumor shrinkage not meeting the RECIST criteria definition of partial response, tumor necrosis and reduction in CA19-9 constituted preliminary evidence of anti-tumor activity. She has experienced no treatment related toxicities thus far and remains on therapy of approximately 3.5 months duration thus far.

Anti-Tumor Activity in Patient 4 Harboring an FGFR2-MGEA5 Fusion, to FGFR Inhibitors.

The FGFR2 fusion partner observed in this patient, MGEA5, is an enzyme responsible for the removal of O-GlcNAc from proteins. Interestingly, soft tissue tumors myxoinflammatory fibroblastic sarcoma (MIFS) and hemosiderotic fibrolipomatous tumor (HFLT) both share a translocation event resulting in rearrangements in TGFBR3 and MGEA5. Associated with this translocation event is the upregulation of NPM3 and FGF8, of which both genes are upregulated in this patient (fold change: NPM3=6.17865, FGF8=1.79769e+308). In breast cancer, grade III tumors had significantly lower MGEA5 expression than grade I tumors with a trend of decreasing expression observed with increasing tumor grade.

FGFR2-TACC3 as a Putative Therapeutic Target

Patient 6 is a 43 year-old white female who underwent a right salpingo-oophorectomy and endometrial ablation in the context of a ruptured ovarian cyst (Table 5). Postoperatively she developed dyspnea and was found to have pulmonary nodules as well as a 5 cm left sided liver mass. Pathological evaluation of the liver mass was consistent with a moderately differentiated intrahepatic cholangiocarcinoma (CK7$^+$, CK20$^-$, TTF-1$^-$) in the absence of any known risk factors (Table 6). She was treated systemically with gemcitabine and cisplatin and had stable disease for approximately 6 months, but was subsequently found to have disease progression. She was treated with FOLFOX for 7 months and again attained stable disease as best response to therapy but eventually experienced disease progression.

Upon disease progression, she was enrolled on a clinical study with the multi-kinase inhibitor pazopanib that is FDA-approved for the treatment of advanced renal cancer or sarcoma—and fortuitously has nanomolar activity against FGFR2 (in vitro IC$_{50}$ to FGFR2≈350 nM) [69]. Transcriptome analysis revealed the presence of an FGFR2-TACC3 fusion (Table 7, FIG. 2). Evaluation of post-pazopanib tissue by immunohistochemistry revealed increased expression of FGFR2 and FGFR3 (FIG. 5) Further evaluation of phosphorylation of downstream targets FRS2 Y436, and ERK (MAPK) revealed strong expression of pERK and moderate expression of pFRS2 Y436 (FIG. 6), confirming activation of the receptor. She had been treated with pazopanib 800 mg orally daily for 4 months and demonstrated tumor shrinkage, which in retrospect, was postulated to be secondary to the FGFR2 inhibitory activity of pazopanib (FIG. 8A).

By RECIST criteria v1.1, the patient had a partial response to therapy as evidenced by a 71% decrease in the sum of diameters. Subsequently, the same patient was treated with a dedicated pan-FGFR inhibitor, ponatinib, (45 mg daily orally; in vitro IC$_{50}$: FGFR1≈24 nM, FGFR2≈8 nM, FGFR3≈8 nM and FGFR4≈34 nM). She again attained minor tumor shrinkage (stable disease by RECIST criteria v1.1, decrease of 4% in sum of largest diameters) in multiple lesions after 2 months of therapy, despite undergoing a 50% dose reduction for abdominal pain felt to be related to drug (FIG. 8B). She remains on therapy approximately 4 months since the initiation of ponatinib. As such, anti-tumor activity was obtained with two distinct FGFR inhibitors in the same patient.

Anti-Tumor Activity in Patient 6, Harboring an FGFR2-TACC3 Fusion, to FGFR Inhibitors.

The FGFR2 fusion partner observed in this patient's tumor, TACC3, is overexpressed in many tumor types with enhanced cell proliferation, migration, and transformation observed in cells overexpressing TACC3. Furthermore regulation of ERK and PI3K/AKT by TACC3 may contribute in part to epithelial-mesenchymal transition (EMT) in cancer, a significant contributor to carcinogenesis. Interestingly, TACC3 has been identified as a fusion partner to FGFR3 in bladder cancer, squamous cell lung cancer, oral cancer, head and neck cancer and glioblastoma multiforme.

ERRFI1 as a Putative Therapeutic Target

Patient 3 was a 50 year-old white male who presented with fevers and night sweats (Table 5). He was found to have a 4 cm tumor in his liver determined to be a poorly differentiated intrahepatic cholangiocarcinoma (CK7$^+$, CK20$^-$, TTF1$^-$, CD56$^-$, synatophysin$^-$, Hep-par 1$^-$) with sclerotic features (Table 6). No overt risk factors for cholangiocarcinoma were identified. A left hepatectomy was undertaken three months later. In addition to the primary tumor in segment 4, limited resections of segments 6 and 8 were undertaken to remove two tumor nodules. He was soon noted to have increased hypermetabolism in the left lower cervical, upper mediastinal and abdomino-retroperitoneal lymph nodes related to metastatic disease from his cholangiocarcinoma. He was treated with gemcitabine and cisplatin for 9 months and obtained stable disease as his best response, followed by eventual progression. He received treatment with pegylated hyaluronidase (PEGPH20) in the setting of an investigational study for one month and had no response to therapy. A biopsy of a left supraclavicular lymph node was obtained two months prior to the initiation of PEGPH20 in the context of a clinical study employing whole genome analysis for putative therapeutic target selection.

Since our study goal was to identify potential therapeutically relevant events, the novel loss of function mutation in ERRFI1 (E384X) detected in Patient 3's metastatic, recurrent/refractory SIC warranted additional examination. Specifically, the allelic fraction of the DNA mutation constituted only 11% of the sequencing reads, is consistent with tissue heterogeneity, and constituted 78% of the sequencing reads within the RNASeq data. Such allele specific expression of the mutated allele from the same tissue specimen suggests nearly complete loss of function of ERRFI1 in this patient's tumor. Notably, the patient's tumor did not harbor any mutations or amplifications in other EGFR signaling members such as EGFR and BRAF.

Upon availability of CLIA validated sequencing data, the patient was treated with erlotinib 150 mg orally/daily. After 3 months, RECIST v1.1 partial response evidenced by a decrease of 58% in the sum of largest diameters was observed (FIG. 9). Evaluation of pretreatment tumor tissue by immunohistochemistry revealed increased expression of EGFR pathway members (FIG. 10).

Discussion

Figure 4:
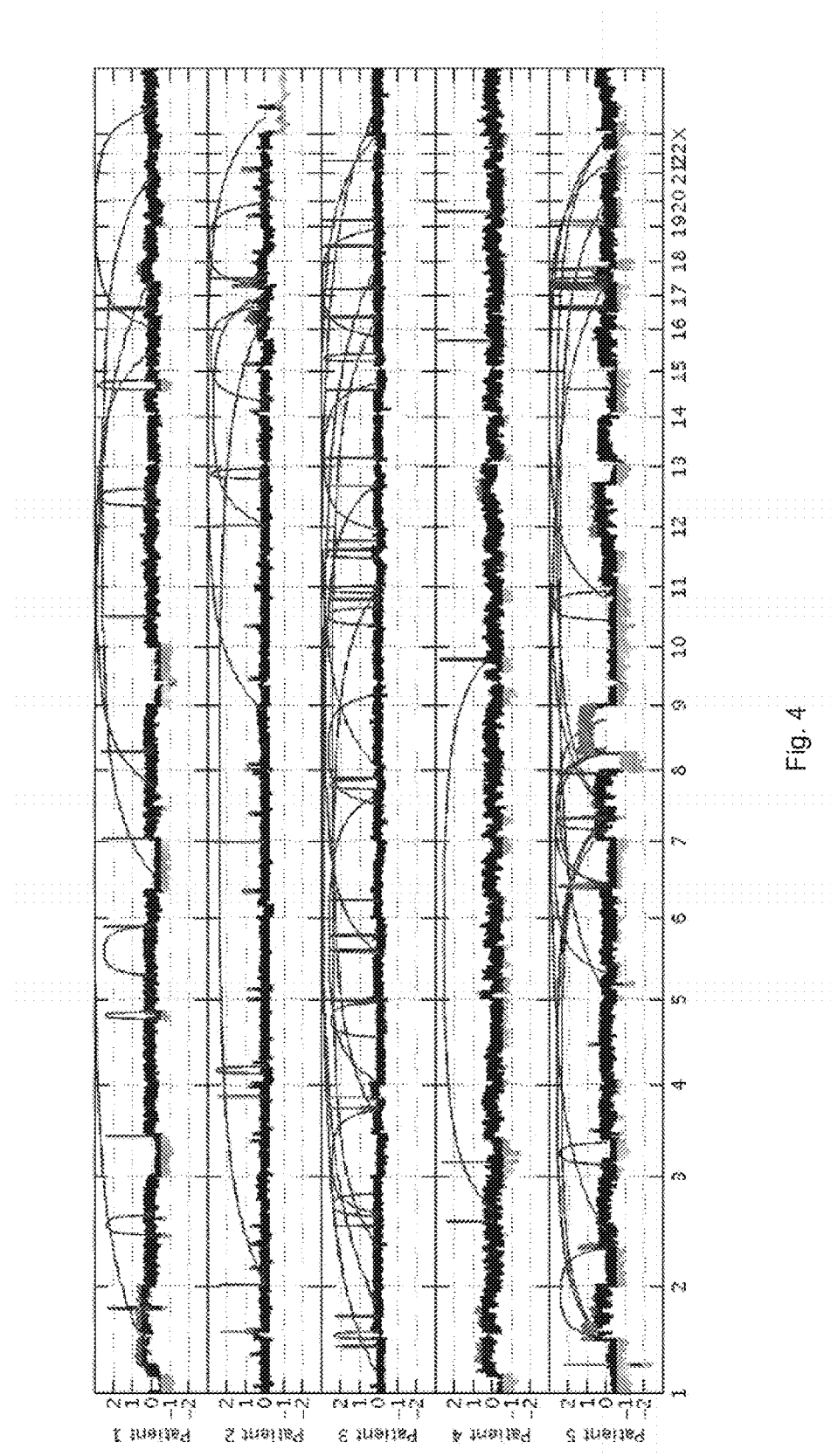
FIG. 4 depicts copy number changes and structural rearrangements. Whole genome data was utilized to determine copy number alterations and structural rearrangements in the genome for Patients 1-5. WGS was not conducted for patient 6. Red indicates copy number gain, green copy number loss and blue lines indicate structural rearrangements. Significant variability between samples was observed for both copy number changes and structural rearrangements. Patient 5 presented with numerous copy number changes and structural rearrangements contrasting with patient 4 who had minimal structural rearrangements and much smaller regions of copy number changes. Patient 3 is characterized by a large number of structural rearrangements with almost no copy number alterations; in contrast, Patient 1 has a moderate number of structural variations, but has large regions of copy number gain and loss. Patient 2 has a moderate number of structural rearrangements with multiple focal amplifications across the genome.

Integrated analysis of sporadic intrahepatic cholangiocarcinoma (SIC) genomic and transcriptomic data led to the discovery of FGFR2 fusion products in three of six assessed patients (Table 7, FIGS. 4 and 11). Members of the FGFR family (FGFR1-4) have been associated with mutations, amplifications and translocation events with oncogenic potential. FGFR fusions with oncogenic activity have been previously identified in bladder cancer (FGFR3), lymphoma (FGFR1 and FGFR3) acute myeloid leukemia (FGFR1), multiple myeloma, myeloproliferative neoplasms, and most recently glioblastoma multiforme (FGFR1 and FGFR3). FGFR2, FGFR3 and FGFR4 have been found to be overexpressed in IDH1/IDH2 mutant biliary cancers, a context seen within Patient 1 in our study (FIG. 5); although, no fusion events were depicted in these studies or in Patient 1.

FGFR2-IIIb Fusion Events.

Although the gene partner fused to FGFR2 was different for each patient (MGEA5, BICC1 and TACC3), the breakpoints in FGFR2 all occurred within the last intron distal to the last coding exon and terminal protein tyrosine kinase domain (FIG. 11). All three fusions were validated at the DNA and/or RNA level (Table 8). Amongst these fusions, the FGFR2-BICC1 fusion has recently been independently identified in SIC. For this particular fusion product we observed, and validated, the presence of two fusion isoforms (FGFR2-BICC1 and BICC1-FGFR2). Interestingly, BICC1 is a negative regulator of Wnt signaling and when comparing expression of tumor and normal tissue we observed differentially expressed Wnt signaling genes, APC (fold change −4.75027), GSK3B (fold change −3.35309), and CTNNB1 (fold change −1.73148), yet when the expression was compared to other cholangiocarincomas, no difference was observed.

TABLE 8

DNA and RNA validation of FGFR2 fusions in 3 patients with advanced sporadic biliary tract cancer.

| Fusion | Annealing site | PCR input | Direction | Pimer sequence |
|---|---|---|---|---|
| FGFR2-MGEA5 | FGFR2 | gDNA | F | 5'-*CTGACTATAACCACGT ACCC*-3' (SEQ ID No. 1) |
| | MGEA5 | gDNA | R | 5'-*AGGGAGAAATTAAAGA ACTTGG*-3' (SEQ ID No. 2) |
| | FGFR2 | cDNA | F | 5'-*TGATGATGAGGGACTG TTG*-3' (SEQ ID No. 3) |
| | MGEA5 | cDNA | R | 5'-*GAGTTCCTTGTCACCA TTTG*-3' (SEQ ID No. 4) |
| FGFR2-BICC1 | FGFR2 | gDNA | F | 5'-*GGCAGAAGAAGAAAGT TGG*-3' (SEQ ID No. 5) |
| | BICC1 | gDNA | R | 5'-*ACTACTGCAGTTTGTT CAAT*-3' (SEQ ID No. 6) |
| | FGFR2 | cDNA | F | 5'-*TGATGATGAGGGACTG TTG*-3' (SEQ ID No. 7) |
| | BICC1 | cDNA | R | 5'-*TGTGTGCTCACAGGAA TAG*-3' (SEQ ID No. 8) |

TABLE 8 -continued

DNA and RNA validation of FGFR2 fusions in 3 patients with advanced sporadic biliary tract cancer.

| Fusion | Annealing site | PCR input | Direction | Pimer sequence |
|---|---|---|---|---|
| BICC1-FGFR2 | BICC1 | cDNA | F | 5' *CGTGGACAGGAAGAAA CT*-3' (SEQ ID No. 9) |
| | FGFR2 | cDNA | R | 5'-*GTGTGGATACTGAGGA AG*-3' (SEQ ID No. 10) |
| FGFR2-TACC3 | FGFR2 | gDNA | F | 5'-*TGACCCCCTAATCTAG TTGC*-3' (SEQ ID No. 11) |
| | TACC3 | gDNA | R | 5'-*AACCTGTCCATGATCT TCCT*-3' (SEQ ID No. 12) |

F-forward,
R-reverse.

DNA and RNA Validation of FGFR2 Fusions in 3 Patients with Advanced Sporadic Biliary Tract Cancer.

The FGFR genes encode multiple structural variants through alternative splicing. Notably, RNASeq data revealed that the FGFR2-IIIb isoform was present in all fusions detected in our study and has been shown to have selectivity for epithelial cells as opposed to the FGFR2-IIIc isoform, which is found selectively in mesenchymal cells. Paradoxically, wildtype FGFR2-IIIb has been described as a tumor suppressor in preclinical systems of bladder cancer and prostate cancer. As such, FGFR signaling appears context-dependent and exhibits variability in disparate tumor types.

Importantly, one critical study has shown that FGFR2 carboxy-terminal deletion mutants induce ligand-independent transformation and clonogenic growth. This is important because all of the fusion events within our study would lead to loss of the carboxy-terminus of FGFR2. Furthermore, a very recent study that described FGFR fusions in solid tumors illustrated that FGFR fusion partners in SIC resulted in dimerization domains, and suggested that activation occurred through ligand independent dimerization and oligomerization. It is likely that both loss of the carboxy terminus and the addition of dimerization domains leads to oncogenic FGFR2 activity in these tumors.

Comparative pathway analysis of genes carrying mutations/aberrant in copy number identified additional potential therapeutic targets belonging to, or intimately integrated with, the EGFR and FGFR signaling pathways (FIG. 3). Interestingly, most of these pathways also have known roles in mediating epithelial-to-mesenchymal cell transitions, which occur frequently during development as well as during tumorigenesis. Patients 3 and 4 harbored aberrations in several genes acting in cadherin signaling pathways, which are important for maintaining cell-cell adhesion.

The preliminary anti-tumor activity noted in a patient with FGFR2-MGEA5 (Patient 4) and FGFR2-TACC3 fusion (Patient 6) represent the first reports of application of FGFR inhibitors to the treatment of patients with cholangiocarcinoma harboring these alterations. These results suggest that oncogenic activation of FGFR2 represent a potential therapeutically actionable event. The FGFR tyrosine kinase inhibitors (TKI) dovitinib and NVP-BGJ398 are currently in clinical development and the FGFR TKI ponatinib was recently approved by the FDA for use in treating T315I mutant chronic myelogenous leukemia. FGF7 (keratinocyte growth factor) has been previously linked to poor prognosis in patients with biliary tract cancer and a small molecule FGFR kinase inhibitor, Ki23057, has demonstrated efficacy in preclinical models. It should be recognized that small molecule tyrosine inhibitors are almost universally promiscuous with regards to specificity and typically significant off-target effects are resultant. Off target efficacy resulting from inhibition of angiogenic kinases in addition to FGFR2 inhibition could explain the anti-tumor activity exhibited in patient 6, as pazopanib has been shown to have nanomolar range potency towards VEGFR1-3, PDGFRA/B and CKIT as well.

The preliminary anti-tumor activity observed in patient 6 with both pazopanib, and subsequently ponatinib, is particularly intriguing, but also raises important questions. There was an initial response to pazopanib, followed by disease progression. This is a phenomenon observed with the clinical application of most targeted therapeutic approaches. Potential explanations include tumor heterogeneity resulting from clonal selection, transcriptional up-regulation of escape pathways, epigenetic mechanisms and other yet undefined mechanisms of resistance to therapy. The patient did not have additional known alterations in key oncogenic pathways in genes such as BRAF, KRAS, EGFR and PIK3CA, which if present, could provide a putative basis for eventual escape from FGFR pathway inhibition. It is unclear why patient 6 initially responded to pazopanib followed by resistance and subsequently responded to ponatinib, another FGFR inhibitor.

Putative explanations include the higher potency of ponatinib observed in vitro to FGFR2 (IC50≈8 nM for ponatinib vs. 350 nM for pazopanib) and resistance being defined as >20% increase in sum of largest diameters per RECIST v1.1 standard criteria that triggered a discontinuation from pazopanib and recapturing of anti-tumor activity by subsequent inhibition of the FGFR pathway which still maintained therapeutic relevance in that patient at a later time point.

Our results suggest immediate and actionable implications for SIC patients with tumors harboring ERFFI1 loss of function mutations or FGFR fusions, given the clinical availability of FDA-approved EGFR and FGFR tyrosine kinase inhibitors. Antibodies specific to FGFR2-IIIb have also shown preclinical efficacy and may serve as an additional platform for therapeutic development in this context. Additional studies to characterize the prevalence of these aberrations in both sporadic and liver fluke associated BTC will need to be conducted. Nevertheless, our results suggest that prospective clinical studies designed to treat patient's tumors harboring these novel genomic aberrations utilizing targeted agents on an individualized basis should be pursued more fully through larger clinical studies in order to explore the precise extent of clinical benefit that this tailored approach may have in patients with primary or advanced BTC.

Additionally, post-treatment biopsies to assess pathway down-regulation in patients 4 and 6 (treated with FGFR inhibitors) and patient 3 (treated with EGFR inhibitor) are not available, as the treatment was not conducted in the setting of a protocol that would allow for the collection of additional research biopsies. Incorporation of post-treatment biopsies in carefully designed prospective studies will be critical towards defining the association between the use of FGFR and EGFR inhibitors in appropriately selected patients with relevant genomic aberrations.

Materials and Methods
Ethics Statement and Sample Collection

Clinical information was assimilated from patient records from the Mayo Clinic. Informed consent was obtained for each patient on two ongoing research protocols approved by the Mayo Clinic Institutional Review Board (10-006180 and 10-002879). Clinicopathological features collected included age, gender, stage, histological grade, sites of metastasis, tumor sample assessment for overall cellularity/necrosis and percent tumor cellularity, prior therapies and risk factors (hepatitis B and C, Caroli's disease, obesity, hepatolithiasis and cholelithiasis, primary sclerosing cholangitis, thorotrast exposure and *H. pylori, H. bilis, S. typhi* and *S. paratyphi* infections). All patients were known to not have had prior exposure to liver flukes that have been implicated in biliary carcinogenesis (*O. viverrini* and *C. sinensis*). Tissue specimens were collected fresh frozen and maintained below −80° C. until nucleic acid extraction. A board certified pathologist who is experienced in biospecimen studies, evaluated a portion of each specimen to confirm the presence of tumor, the degree of necrosis and the percent cellularity.

Whole Genome Sequencing
Patients 1, 3, 4, and 5

1.1 µg genomic DNA was used to generate separate long insert whole genome libraries for each sample using Illumina's (San Diego, Calif.) TruSeq DNA Sample Prep Kit (catalog# FC-121-2001). In summary, genomic DNAs are fragmented to a target size of 900-1000 bp on the Covaris E210. 100 ng of the sample was run on a 1% TAE gel to verify fragmentation. Samples were end repaired and purified with Ampure XP beads using a 1:1 bead volume to sample volume ratio, and ligated with indexed adapters. Samples are size selected at approximately 1000 bp by running samples on a 1.5% TAE gel and purified using Bio-Rad Freeze 'n Squeeze columns and Ampure XP beads. Size selected products are then amplified using PCR and products were cleaned using Ampure XP beads.

Patient 2

300 ng genomic tumor and normal DNA was used to create whole genome libraries. Samples were fragmented on the Covaris E210 to a target size of 200-300 bp and 50 ng of the fragmented product was run on a 2% TAE gel to verify fragmentation. Whole genome libraries were prepared using Illumina's TruSeq DNA Sample Prep Kit.

Exome Sequencing
Patients 1 and 3

1.1 µg genomic DNA for each sample was fragmented to a target size of 150-200 bp on the Covaris E210. 100 ng of fragmented product was run on TAE gel to verify fragmentation. The remaining 1 µg of fragmented DNA was prepared using Agilent's SureSelect$^{XT}$ and SureSelect$^{XT}$ Human All Exon 50 Mb kit (catalog# G7544C).

Patient 2

50 ng genomic tumor and normal DNA was used to create exome libraries using Illumina's Nextera Exome Enrichment kit (catalog# FC-121-1204) following the manufacturer's protocol.

Patients 4 and 5

1 µg of each tumor and germline DNA sample was used to generate separate exome libraries. Libraries were prepared using Illumina's TruSeq DNA Sample Prep Kit and Exome Enrichment Kit (catalog# FC-121-1008) following the manufacturer's protocols.

Patient 6

3 µg of genomic tumor and normal DNA was fragmented on the Covaris E210 to a target size of 150-200 bp. Exome libraries were prepared with Agilent's (Santa Clara, Calif.) SureSelectXT Human All Exon V4 library preparation kit (catalog#5190-4632) and SureSelectXT Human All Exon V4+UTRs (catalog#5190-4637) following the manufacturer's protocols.

RNA Sequencing

Patients 1, 2 and 3

50 ng total RNA was used to generate whole transcriptome libraries for RNA sequencing. Using the Nugen Ovation RNA-Seq System v2 (catalog#7102), total RNA was used to generate double stranded cDNA, which was subsequently amplified using Nugen's SPIA linear amplification process. Amplified products were cleaned using Qiagen's QIAquick PCR Purification Kit and quantitated using Invitrogen's Quant-iT Picogreen. 1 µg of amplified cDNA was fragmented on the Covaris E210 to a target size of 300 bp. Illumina's TruSeq DNA Sample Preparation Kit was used to prepare libraries from 1 µg amplified cDNA.

Patients 4, 5 and 6

1 µg of total RNA for each sample was used to generate RNA sequencing libraries using Illumina's TruSeq RNA Sample Prep Kit V2 (catalog# RS-122-2001) following the manufacturer's protocol.

Paired End Sequencing

Libraries with a 1% phiX spike-in were used to generate clusters on HiSeq Paired End v3 flowcells on the Illumina cBot using Illumina's TruSeq PE Cluster Kit v3 (catalog# PE-401-3001). Clustered flowcells were sequenced by synthesis on the Illumina HiSeq 2000 using paired-end technology and Illumina's TruSeq SBS Kit.

Alignment and Variant Calling

Whole Genome and Whole Exome

For whole genome and exome sequencing fastq files were aligned with BWA 0.6.2 to GRCh37.62 and the SAM output were converted to a sorted BAM file using SAMtools 0.1.18. BAM files were then processed through indel realignment, mark duplicates, and recalibration steps in this order with GATK 1.5 where dpsnp135 was used for known SNPs and 1000 Genomes' ALL.wgs.low_coverage_vqsr.20101123 was used for known indels. Lane level sample BAMs were then merged with Picard 1.65 if they were sequenced across multiple lanes. Comparative variant calling for exome data was conducted with Seurat [22].

Previously described copy number and translocation detection were applied to the whole genome long insert sequencing data and these are made available through the Internet site github.com/davcraig75/tgen_somaticSV.

Copy number detection was based on a log 2 comparison of normalized physical coverage (or clonal coverage) across tumor and normal whole genome long-insert sequencing data, where physical coverage was calculated by considering the entire region a paired-end fragment spans on the genome, then the coverage at 100 bp intervals was kept. Normal and tumor physical coverage was then normalized, smoothed and filtered for highly repetitive regions prior to calculating the log 2 comparison. Translocation detection was based on discordant read evidence in the tumor whole genome sequencing data compared to its corresponding normal data. In order for the structural variant to be called there needs to be greater than 7 read pairs mapping to both sides of the breakpoint. The unique feature of the long-insert whole-genome sequencing was the long overall fragment size (~1 kb), where by two 100 bp reads flank a region of ~800 bp. The separation of forward and reverse reads increases the overall probability that the read pairs do not cross the breakpoint and confound mapping.

RNA

For RNA sequencing, lane level fastq files were appended together if they were across multiple lanes. These fastq files were then aligned with TopHat 2.0.6 to GRCh37.62 using ensembl.63.genes.gtf as GTF file. Changes in transcript expression were calculated with Cuffdiff 2.0.2. For novel fusion discovery reads were aligned with TopHat-Fusion 2.0.6 [23] (patients 2, 3, 4 and 6). In addition, Chimerascan 0.4.5 [24] was used to detect fusions in patient 1, deFuse 5.0 [25] used in patients 2, 3 and 5 and SnowShoes [26] for patients 2 and 5.

Somatic Mutation Validation

Mutations of potential clinical relevance were confirmed in a Clinical Laboratory Improvement Amendments (CLIA) laboratory with Sanger sequencing or quantitative PCR.

Immunohistochemistry

The immunohistochemistry was performed following the procedures described previously [27]. Briefly, slides were dewaxed, rehydrated and antigen retrieved on-line on the BondMax autostainer (Leica Microsystems, INC Bannockburn, Ill.). Slides were then subjected to heat-induced epitope retrieval using a proprietary EDTA-based retrieval solution. Endogenous peroxidase was then blocked and slides were incubated with the following antibodies: FGFR2 (BEK, Santa Cruz, catalog# sc-20735), FGFR3 (C-15, Santa Cruz, catalog# sc-123), panAKT (Cell Signaling Technology, catalog#4685, pAKT (Cell Signaling Technology, catalog#4060), EGFR (Cell Signaling Technology, catalog#4267, pEGFR (Cell Signaling Technology, catalog#2234), MAPK/ERK1/2 (Cell Signaling Technology, catalog#4695), pMAPK/pERK (Cell Signaling Technology, catalog#4376) and pFRS2 Y436 (Abcam, catalog# ab78195). Sections were visualized using the Polymer Refine Detection kit (Leica) using diaminobenzidine chromogen as substrate.

Fluorescent In-Situ Hybridization (FISH)

FISH was performed on formalin-fixed paraffin-embedded (FFPE) specimens using standard protocols and dual-color break-apart rearrangement probes specific to the FGFR2 gene (Abbott Molecular, Inc. Des Plaines, Ill.) located at 10q26. The 5' FGFR2 signal was labeled with Spectrum Orange (orange) and the 3' FGFR2 signal was labeled with Spectrum Green (green).

The experiments above are based on a study designed to look at tumor/normal exome, including deep coverage of coding regions and point mutations (SNPs, indels, etc.) as well as structural variants in non-coding regions like translocations, inversions, etc. Tumor/reference RNA-seq experiments also were designed for examination of differential expression and gene fusions. These experiments show that mutation of ERRFI1 is a biomarker for cancers responsive to EGFR inhibitors, such as erlotinib.

The claims are not intended to be limited to the materials, methods, embodiments and examples described herein.

REFERENCES

1. Shin H R, Lee C U, Park H J, Seol S Y, Chung J M, et al. (1996) Hepatitis B and C virus, *Clonorchis sinensis* for the risk of liver cancer: a case-control study in Pusan, Korea. International journal of epidemiology 25: 933-940.
2. Watanapa P (1996) Cholangiocarcinoma in patients with opisthorchiasis. The British journal of surgery 83: 1062-1064.
3. Watanapa P, Watanapa W B (2002) Liver fluke-associated cholangiocarcinoma. The British journal of surgery 89: 962-970.

4. Bergquist A, Ekbom A, Olsson R, Kornfeldt D, Loof L, et al. (2002) Hepatic and extrahepatic malignancies in primary sclerosing cholangitis. Journal of hepatology 36: 321-327.
5. Bergquist A, Glaumann H, Persson B, Broome U (1998) Risk factors and clinical presentation of hepatobiliary carcinoma in patients with primary sclerosing cholangitis: a case-control study. Hepatology 27: 311-316.
6. Burak K, Angulo P, Pasha T M, Egan K, Petz J, et al. (2004) Incidence and risk factors for cholangiocarcinoma in primary sclerosing cholangitis. The American journal of gastroenterology 99: 523-526.
7. Claessen M M, Vleggaar F P, Tytgat K M, Siersema P D, van Buuren H R (2009) High lifetime risk of cancer in primary sclerosing cholangitis. Journal of hepatology 50: 158-164.
8. Visser B C, Suh I, Way L W, Kang S M (2004) Congenital choledochal cysts in adults. Archives of surgery 139: 855-860 discussion 860-852.
9. Hsing A W, Zhang M, Rashid A, McGlynn K A, Wang B S, et al. (2008) Hepatitis B and C virus infection and the risk of biliary tract cancer: a population-based study in China. International journal of cancer Journal international du cancer 122: 1849-1853.
10. Kobayashi M, Ikeda K, Saitoh S, Suzuki F, Tsubota A, et al. (2000) Incidence of primary cholangiocellular carcinoma of the liver in Japanese patients with hepatitis C virus-related cirrhosis. Cancer 88: 2471-2477.
11. Liu X F, Zou S Q, Qiu F Z (2003) Pathogenesis of cholangiocarcinoma in the porta hepatis and infection of hepatitis virus. Hepatobiliary & pancreatic diseases international: HBPD INT 2: 285-289.
12. Shaib Y H, El-Serag H B, Davila J A, Morgan R, McGlynn K A (2005) Risk factors of intrahepatic cholangiocarcinoma in the United States: a case-control study. Gastroenterology 128: 620-626.
13. Welzel T M, Graubard B I, El-Serag H B, Shaib Y H, Hsing A W, et al. (2007) Risk factors for intrahepatic and extrahepatic cholangiocarcinoma in the United States: a population-based case-control study. Clinical gastroenterology and hepatology: the official clinical practice journal of the American Gastroenterological Association 5: 1221-1228.
14. Yamamoto S, Kubo S, Hai S, Uenishi T, Yamamoto T, et al. (2004) Hepatitis C virus infection as a likely etiology of intrahepatic cholangiocarcinoma. Cancer science 95: 592-595.
15. Donato F, Gelatti U, Tagger A, Favret M, Ribero M L, et al. (2001) Intrahepatic cholangiocarcinoma and hepatitis C and B virus infection, alcohol intake, and hepatolithiasis: a case-control study in Italy. Cancer causes & control: CCC 12: 959-964.
16. Lee C C, Wu C Y, Chen G H (2002) What is the impact of coexistence of hepatolithiasis on cholangiocarcinoma? Journal of gastroenterology and hepatology 17: 1015-1020.
17. Becker N, Liebermann D, Wesch H, Van Kaick G (2008) Mortality among Thorotrast-exposed patients and an unexposed comparison group in the German Thorotrast study. European journal of cancer 44: 1259-1268.
18. Travis L B, Hauptmann M, Gaul L K, Storm H H, Goldman M B, et al. (2003) Site-specific cancer incidence and mortality after cerebral angiography with radioactive thorotrast. Radiation research 160: 691-706.
19. Khan S A, Thomas H C, Davidson B R, Taylor-Robinson S D (2005) Cholangiocarcinoma. Lancet 366: 1303-1314.
20. Valle J, Wasan H, Palmer D H, Cunningham D, Anthoney A, et al. (2010) Cisplatin plus gemcitabine versus gemcitabine for biliary tract cancer. The New England journal of medicine 362: 1273-1281.
21. Craig D W, O'Shaughnessy J A, Kiefer J A, Aldrich J, Sinari S, et al. (2013) Genome and transcriptome sequencing in prospective metastatic triple-negative breast cancer uncovers therapeutic vulnerabilities. Mol Cancer Ther 12: 104-116.
22. Christoforides A, Carpten J D, Weiss G J, Demeure M J, Von Hoff D D, et al. (2013) Identification of somatic mutations in cancer through Bayesian-based analysis of sequenced genome pairs. BMC Genomics 14: 302.
23. Kim D, Salzberg S L (2011) TopHat-Fusion: an algorithm for discovery of novel fusion transcripts. Genome Biol 12: R72.
24. Iyer M K, Chinnaiyan A M, Maher C A (2011) ChimeraScan: a tool for identifying chimeric transcription in sequencing data. Bioinformatics 27: 2903-2904.
25. McPherson A, Hormozdiari F, Zayed A, Giuliany R, Ha G, et al. (2011) deFuse: an algorithm for gene fusion discovery in tumor RNA-Seq data. PLoS Comput Biol 7: e1001138.
26. Asmann Y W, Hossain A, Necela B M, Middha S, Kalari K R, et al. (2011) A novel bioinformatics pipeline for identification and characterization of fusion transcripts in breast cancer and normal cell lines. Nucleic Acids Res 39: e100.
27. Diep C H, Zucker K M, Hostetter G, Watanabe A, Hu C, et al. (2012) Down-regulation of Yes Associated Protein 1 expression reduces cell proliferation and clonogenicity of pancreatic cancer cells. PLoS One 7: e32783.

The invention claimed is:

1. A method of treating biliary tract cancer, comprising the steps of: analyzing a patient tumor sample for a mutation in ERRFI1 wherein said mutation in ERRFI1 comprises E384X; and treating said patient with an inhibitor of Epidermal Growth Factor Receptor (EGFR) if said mutation is present.

2. The method of claim 1, wherein said biliary tract cancer is a cholangiocarcinoma.

3. The method of claim 2, wherein said EGFR inhibitor is selected from the group containing erlotinib and gefitinib.

4. The method of claim 1, wherein said EGFR inhibitor is selected from the group containing erlotinib and gefitinib.

5. The method of claim 1, wherein said analyzing step comprises subjecting the patient tumor sample to amplification and exome sequencing.

6. The method of claim 1, further including assessing effects on said cancer through tomography following a course of treatment.

7. A method of inhibiting biliary tract cancer cell growth, comprising contacting a biliary tract cancer cell containing a mutation in ERRFI1 with an Epidermal Growth Factor Receptor (EGFR) inhibitor, wherein said mutation in ERRFI1 comprises E384X.

8. The method of claim 7, wherein said biliary tract cancer is a cholangiocarcinoma.

9. The method of claim 7, wherein said EGFR inhibitor is selected from the group containing erlotinib and gefitinib.

10. The method of claim 7, wherein said inhibitor is erlotinib at a dosage of about 150 mg orally per day.

11. The method of claim 7, wherein said mutation in ERRFI1 is confirmed through exome sequencing.

12. The method of claim 7, further including assessing growth inhibition through tomography following a course of treatment.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Primer Sequence

<400> SEQUENCE: 1
ctgactataa ccacgtaccc                                              20

<210> SEQ ID NO 2
<211> LENGTH: 22

<212> TYPE: DNA
<213> ORGANISM: Artificial Sequence
<220> FEATURE:
<223> OTHER INFORMATION: Primer Sequence

<400> SEQUENCE: 2
agggagaaat taaagaactt gg                                        22

<210> SEQ ID NO 3
<211> LENGTH: 19
<212> TYPE: DNA
<213> ORGANISM: Artificial Sequence
<220> FEATURE:
<223> OTHER INFORMATION: Primer Sequence

<400> SEQUENCE: 3
tgatgatgag ggactgttg                                            19

<210> SEQ ID NO 4
<211> LENGTH: 20
<212> TYPE: DNA
<213> ORGANISM: Artificial Sequence
<220> FEATURE:
<223> OTHER INFORMATION: Primer Sequence

<400> SEQUENCE: 4
gagttccttg tcaccatttg                                           20

<210> SEQ ID NO 5
<211> LENGTH: 19
<212> TYPE: DNA
<213> ORGANISM: Artificial Sequence
<220> FEATURE:
<223> OTHER INFORMATION: Primer Sequence

<400> SEQUENCE: 5
ggcagaagaa gaaagttgg                                            19

<210> SEQ ID NO 6
<211> LENGTH: 20
<212> TYPE: DNA
<213> ORGANISM: Artificial Sequence
<220> FEATURE:
<223> OTHER INFORMATION: Primer Sequence

<400> SEQUENCE: 6
actactgcag tttgttcaat                                           20

<210> SEQ ID NO 7
<211> LENGTH: 19
<212> TYPE: DNA
<213> ORGANISM: Artificial Sequence
<220> FEATURE:
<223> OTHER INFORMATION: Primer Sequence

<400> SEQUENCE: 7
tgatgatgag ggactgttg                                            19

<210> SEQ ID NO 8
<211> LENGTH: 19
<212> TYPE: DNA
<213> ORGANISM: Artificial Sequence
<220> FEATURE:
<223> OTHER INFORMATION: Primer Sequence

<400> SEQUENCE: 8

```
-continued tgtgtgctca caggaatag                                                    19

<210> SEQ ID NO 9
<211> LENGTH: 18
<212> TYPE: DNA
<213> ORGANISM: Artificial Sequence
<220> FEATURE:
<223> OTHER INFORMATION: Primer Sequence

<400> SEQUENCE: 9
cgtggacagg aagaaact                                                     18

<210> SEQ ID NO 10
<211> LENGTH: 18
<212> TYPE: DNA
<213> ORGANISM: Artificial Sequence
<220> FEATURE:
<223> OTHER INFORMATION: Primer Sequence

<400> SEQUENCE: 10
gtgtggatac tgaggaag                                                     18

<210> SEQ ID NO 11
<211> LENGTH: 20
<212> TYPE: DNA
<213> ORGANISM: Artificial Sequence
<220> FEATURE:
<223> OTHER INFORMATION: Primer Sequence

<400> SEQUENCE: 11
tgacccccta atctagttgc                                                   20

<210> SEQ ID NO 12
<211> LENGTH: 20
<212> TYPE: DNA
<213> ORGANISM: Artificial Sequence
<220> FEATURE:
<223> OTHER INFORMATION: Primer Sequence

<400> SEQUENCE: 12
aacctgtcca tgatcttcct                                                   20
```